United States Patent
Nudelman et al.

(10) Patent No.: US 9,334,272 B2
(45) Date of Patent: May 10, 2016

(54) DERIVATIVES OF PURINIC AND PYRIMIDINIC ANTIVIRAL AGENTS AND USE THEREOF AS POTENT ANTICANCER AGENTS

(71) Applicants: Ramot at Tel-Aviv University Ltd., Tel-Aviv (IL); Bar-Ilan University, Ramat-Gan (IL)

(72) Inventors: Abraham Nudelman, Rechovot (IL); Ada Rephaeli, Herzlia (IL)

(73) Assignees: Ramot at Tel-Aviv University Ltd., Tel-Aviv (IL); Bar-Ilan University, Ramat Gan (IL)

( * ) Notice: Subject to any disclaimer, the term of this patent is extended or adjusted under 35 U.S.C. 154(b) by 0 days.

(21) Appl. No.: 14/339,491

(22) Filed: Jul. 24, 2014

(65) Prior Publication Data

US 2014/0371245 A1 Dec. 18, 2014

Related U.S. Application Data

(63) Continuation of application No. 12/450,477, filed as application No. PCT/IL2008/000443 on Mar. 30, 2008, now abandoned.

(60) Provisional application No. 60/920,820, filed on Mar. 30, 2007.

(51) Int. Cl.
*A61K 31/522* (2006.01)
*C07D 473/18* (2006.01)

(52) U.S. Cl.
CPC .................................. *C07D 473/18* (2013.01)

(58) Field of Classification Search
None
See application file for complete search history.

(56) References Cited

U.S. PATENT DOCUMENTS 4,816,447 A * 3/1989 Ashton et al. .................... 514/81
2011/0028497 A1 2/2011 Nudelman et al.

FOREIGN PATENT DOCUMENTS

| EP | 0165164 | 12/1985 |
|---|---|---|
| WO | WO 2005/120577 | 12/2005 |
| WO | WO 2008/120205 | 10/2008 |

OTHER PUBLICATIONS

Communication Pursuant to Article 94(3) EPC Dated Aug. 6, 2012 From the European Patent Office Re. Application No. 08856542.9.
Communication Pursuant to Article 94(3) EPC Dated May 17, 2013 From the European Patent Office Re. Application No. 08720061.4.
Communication Pursuant to Article 94(3) EPC Dated Feb. 21, 2014 From the European Patent Office Re. Application No. 08720061.4.
International Preliminary Report on Patentability Dated Oct. 15, 2009 From the International Bureau of WIPO Re. Application No. PCT/IL2008/000443.
International Search Report and the Written Opinion Dated Aug. 29, 2008 From the International Searching Authority Re. Application No. PCT/IL2008/000443.
Official Action Dated Apr. 3, 2012 From the US Patent and Trademark Office Re. U.S. Appl. No. 12/450,477.
Official Action Dated Oct. 18, 2011 From the US Patent and Trademark Office Re. U.S. Appl. No. 12/450,477.
Official Action Dated Mar. 25, 2014 From the US Patent and Trademark Office Re. U.S. Appl. No. 12/450,477.
Ageberg et al. "The Histone Deacetylase Inhibitor Valproic Acid Sensitizes Diffuse Large B-Cell Lymphoma Cell Lines to CHOP-Induced Cell Death", American Journal of Translational Research, 5(2): 170-183, Epub Mar. 28, 2013.
Arce et al. "A Proof-of-Principle Study of Epigenetic Therapy Added to Neoadjuvant Doxorubicin Cyclophosphamide for Locally Advanced Breast Cancer", PLoS ONE, 1(1): e98-1-e98-11, Dec. 20, 2006.
Aune et al. "Selective Inhibition of Class I But Not Class IIb Histone Deacetylases Exerts Cardiac Protection From Ischemia Reperfusion", Journal of Molecular and Cellular Cardiology, 72: 138-145, Available Online Mar. 13, 2014.
Blaheta et al. "Valproic Acid inhibits Adhesion of Vincristine- and Cisplatin-Resistant Neuroblastoma Tumour Cells to Endothelium", British Journal of Cancer, 96: 1699-1706, Published Online May 15, 2007.
Candelaria et al. "A Phase II Study of Epigenetic Therapy With Hydralazine and Magnesium Valproate to Overcome Chemotherapy Resistance in Refractory Solid Tumors", Annals of Oncology, 18(9): 1529-1538, Sep. 2007.
Carraway et al. "Addition of Histone Deacetylase Inhibitors in Combination Therapy", Journal of Clinical Oncology, 25(15): 1955-1956, May 20, 2007.
Catalano et al. "Valproic Acid, a Histone Deacetylase Inhibitor, Enhances Sensitivity to Doxorubicin in Anaplastic Thyroid Cancer Cells", Journal of Endocrinology, 191: 465-472, 2006.
Chavez-Blanco et al. "Antineoplastic Effects of the DNA Methylation Inhibitor Hydralazine and the Histone Deacetylase Inhibitor Valproic Acid in Cancer Cell Lines", Cancer Cell International, 6(2): 1-9, Jan. 31, 2006.
Chodurek et al. "Valproic Acid Enhances Cisplatin Cytotoxicity in Melanona Cells", Acta Poloniae Pharmaceutica—Drug Research, 69(6): 1298-1302, 2012.
Cipro et al. "Valproic Acid Overcomes Hypoxia-Induced Resistance to Apoptosis", Oncology Reports, 27: 1219-1226, 2012.
Daosukho et al. "Phenylbutyrate, a Histone Deacetylase Inhibitor, Protects Agaisnt Adriamycin-Induced Cardiac Injury", Free Radical Biology & Medicine, 42(12): 1818-1825, Jun. 15, 2007.
Gao et al. "NMR Spectral Data for Acyclovir Prodrugs", Magnetic Resonance in Chemistry, 37: 687-689, 1999.

(Continued)

*Primary Examiner* — Craig Ricci

(57) ABSTRACT

Novel N-acylated, O-acylated and (bis or tris)-N,O-acylated derivatives of purinic and pyrimidinic nucleoside analogs, pharmaceutical compositions containing same, and uses thereof for treating proliferative diseases or disorders are disclosed.

10 Claims, 16 Drawing Sheets
(4 of 16 Drawing Sheet(s) Filed in Color)

(56) References Cited

OTHER PUBLICATIONS

Gao et al. "NMR Spectral Data for Ester Prodrugs of Ganciclovir", Magnetic Resonance in Chemistry, 38: 696-700, 2000.
Gao et al. "Regioselective Synthesis of Acyclovir and Its Various Prodrugs", Synthetic Communications, 31(9): 1399-1419, Jan. 2001.
Jain et al. "Auto-Acetylation Stabilizes P300 in Cardiac Myocytes During Acute Oxidative Stress, Promoting STAT3 Accumulation and Cell Survival", Breast Cancer Research and Treatment, 135: 103-114, Published Online May 5, 2012.
Jambalganiin et al. "A Novel Mechanism for Inhibition of Lipopolysaccharide-Induced Proinflammatory Cytokine Production by Valproic Acid", International Immunopharmacology, 20: 181-187, Available Online Mar. 12, 2014.
Kee et al. "HDAC Inhibition Suppresses Cardiac Hypertrophy and Fibrosis in DOCA-Salt Hypertensive Rats Via Regulation of HDAC6/HDAC8 Enzyme Activity", Kidney & Blood Pressure Research, 37: 229-239, Published Online Jul. 8, 2013.
Kessler-Icekson et al. "A Histone Deacetylase Inhibitory Prodrug—Butyroyloxymethyl Diethyl Phosphate—Protects the Heart and Cardiomyocytes Against Ischeinia Injury", European Journal of Pharmaceutical Sciences, 45: 592-599, Available Online Jan. 3, 2012.
Kim et al. "Efficacy on Anaplastic Thyroid Carcinoma of Valproic Acid Alone or in Combination With Doxorubicin, a Synthetic Chenodeoxycholic Acid Derivative, or Lactacystin", International Journal of Oncology, 34: 1353-1362, 2009.
Marchion et al. "In Vivo Synergy Between Topoisomerase II and Histone Deacetylase Inhibitors: Predictive Correlates", Molecular Cancer Therapy, 4(12): 1993-2000, Dec. 2005.
Moattari et al. "Sodium Valproate-Induced Potentiation of Antiherpetic Effect of Acyclovir", Iranian Journal of Medical Sciences, IJMS, 27(4): 180-187, Dec. 2002.
Munster et al. "Clinical and Biological Effects of Valproic Acid as a Histone Deacetylase Inhibitor on Tumor and Surrogate Tissues: Phase I/II Trial on Valproic Acid and Epirubicin/FEC", Clinical Cancer Research, 15(7): 2488-2496, Apr. 1, 2009.
Munster et al. "Phase I Trial of Histone Deacetylase Inhibition by Valproic Acid Followed by the Topoisomerase II Inhibitor Epirubicin in Advanced Solid Tumors: A Clinical and Translational Study", Journal of Clinical Oncology, 25(15): 1979-1985, May 20, 2007.
Noguchi et al. "Successful Treatment of Anaplastic Thyroid Carcinoma With a Combination of Oral Valproic Acid, Chemotherapy, Radiation and Surgery", Endocrine Journal, 56(2): 245-249, 2009.
Rephaeli et al. "Anticancer Prodrugs of Butyric Acid and Formaldehyde Protect Against Doxorubicin-Induced Cardiotoxicity", British Journal of Cancer, 96: 1667-1674, Published Online May 1, 2007.
Rodriguez-Menendez et al. "Valproate Protective Effects on Cisplatin-Induced Peripheral Neuropathy: An in Vitro and in Vivo Study", Anticancer Research, 28: 335-342, 2008.
Sanchez-Gonzales et al. "Antileukemia Activity of the Combination of an Anthracycline With a Histone Deacetylase Inhibitor", Blood, 108(4): 1174-1182, Aug. 15, 2006.
Scherpereel et al. "Valproate-Doxorubicin: Promising Therapy for Progressing Mesothelioma. A Phase II Study", European Respiratory Journal, 37(1): 129-135, Published Online Jun. 7, 2010.
Schuchmann et al. "Histone Deacetylase Inhibition by Valproic Acid Down-Regulates C-FLIP/CASH and Sensitizes Hepatoma Cells Towards CD95- and TRAIL Receptor-Mediated Apoptosis and Chemotherapy", Oncology Reports, 15: 227-230, 2006.

Sinn et al. "Valproic Acid-Mediated Neuroprotection in Intracerebral Hemorrhage Via Histone Deacetylase Inhibition and Transcriptional Activation", Neurobiology of Disease, 26: 464-472, Available Online Feb. 23, 2007.
Suh et al. "Histone Deacetylase Inhibitors Suppress the Expression of Inflammatory and Innate Immune Response Genes in Human Microglia and Astrocytes", Journal of Neuroimmune Pharmacology, 5(4): 521-532, Dec. 2010.
Tao et al. "Histone Deacetylase n Cardiac Fibrosis: Current Perspectives for Therapy", Cellular Signalling, 26: 521-527, Available Online Dec. 7, 2013.
Tarasenko et al. "A Novel Valproic Acid Prodrug as an Anticancer Agent That Enhances Doxorubicin Anticancer Activity and Protects Normal Cells Against Its Toxicity in Vitro and in Vivo", Biochemical Pharmacology, 88: 158-168, Available Online Jan. 24, 2014.
Tarasenko et al. "Disparate Impact of Butyroyloxymethyl Diethylphosphate (AN-7), A Histone Deacetylase Inhibitor, and Doxorubicin in Mice Bearing a Mammary Tumor", PLoS One, 7(2): e31393-1-e31393-13, Feb. 23, 2012.
Tarasenko et al. "The Histone Deacetylase Inhibitor Butyroyloxymethyl Diethylphosphate (AN-7) Protects Cells Against Toxicity of Anticancer Agents While Augmenting Their Anticancer Activity", Investigational New Drugs, 30(1): 130-143, Published Online Sep. 23, 2010.
Thurn et al. "Rational Therapeutic Combinations With Histone Deacetylase Inhibitors for the Treatment of Cancer", Future Oncology, 7(2): 263-283, Feb. 2011.
Valentini et al. "Valproic Acid Induces Apoptosis, P[16INK4A] Upregulation and Sensitization to Chemotherapy in Human Melanoma Cells", Cancer Biology & Therapy, 6(2): e1-e7, Published Online Feb. 1, 2007.
Van Beneden et al. "Comparison of Trichostatin A and Valproic Acid Treatment Regimens in a Mouse Model of Kidney Fibrosis", Toxicology and Applied Pharmacology, 271: 276-284, Available Online May 22, 2013.
Van Beneden et al. "Valproic Acid Attenuates Proteinuria and Kidney Injury", Journal of the American Society of Nephrology, 22: 1863-1875, 2011.
Vandermeers et al. "Valproate, in Combination With Pemetrexed and Cisplatin, Provides Additional Efficacy to the Treatment of Malignant Mesothelioma", Clinical Cancer Research, 15(8): 2818-2828, Published Online Apr. 7, 2009.
Wang et al. "FGF-2 Protects Cardiomyocytes From Doxorubicin Damage Via Protein Kinase C-Dependent Effects on Efflux Transporters", Cardiovascular Research, 98: 56-63, Published Online Jan. 22, 2013.
Wang et al. "Inhibitory Effect of Valproic Acid on Bladder Cancer in Combination With Chemotherapeutic Agents in Vitro and in Vivo", Oncology Letters, 6: 1492-1498, 2013.
Wittenburg et al. "Phase I Pharmacokinetic and Pharmacodynamic Evaluation of Combined Valproic Acid/Doxorubicin Treatment in Dogs With Spontaneous Cancer", Clinical Cancer Research, 16(19): 4832-4842, Oct. 1, 2010.
Wittenburg et al. "The Histone Deacetylase Inhibitor Valproic Acid Sensitizes Human and Canine Osteosarcoma to Doxorubicin", Cancer Chemotherapy and Pharmacology, 67(1): 83-92, Jan. 2011.
Hrebackova et al. "Valproic Acid in the Complex Therapy of Malignant Tumors", Current Drug Targets, 11(3): 361-379, Mar. 2010. Abstract.

* cited by examiner

DERIVATIVES OF PURINIC AND PYRIMIDINIC ANTIVIRAL AGENTS AND USE THEREOF AS POTENT ANTICANCER AGENTS

RELATED APPLICATIONS

This application is a continuation of U.S. patent application Ser. No. 12/450,477 filed on Sep. 28, 2009, which is a National Phase of PCT Patent Application No. PCT/IL2008/000443 having International Filing Date of Mar. 30, 2008, which claims benefit of priority of U.S. Provisional Patent Application No. 60/920,820 filed on Mar. 30, 2007. The contents of the above applications are all incorporated herein by reference.

FIELD AND BACKGROUND OF THE INVENTION

The present invention, in some embodiments thereof, relates to novel compounds and, more particularly, but not exclusively, to derivatives of nucleoside analogs which can be used in anti-cancer therapy.

Oncogenic viruses are estimated to be involved in about 16% of neoplasia. They are estimated to be involved in 10% of cases in high-income countries to 25% in Africa. However, there are some cancer types for which a viral origin is suspected, although not conclusively proven, therefore it is likely that these percentages are underestimates.

Epidemiological and molecular data support the notion that viruses are involved in processes of cell transformation and oncogenesis. The mechanism proposed for tumorigenesis by SV40 is related to viral oncoproteins, the large T antigen (Tag) and the small t antigen (tag). Tag acts mainly by blocking the functions of p53 and RB tumor suppressor proteins, as well as by inducing chromosomal aberrations in the host cell. These chromosome alterations may hit genes which play an important role in oncogenesis and generate genetic instability in tumor cells. The chromosome damage in the infected cells may explain the low viral load in SV40-positive human tumors and the observation that Tag is expressed only in a fraction of tumor cells. "Hit and run" seems the most plausible mechanism to explain this situation. Some supporting evidence for the implication of viruses in prostate carcinoma show prevalence of polyomaviruses in 19% of prostate cancer cases. Moreover, individuals harboring mutations or variants that impair function of ribonuclease L, known to play a role in defense against viral infection, were found to be susceptible to prostate cancer and a survey of 86 tumors by specific RT-PCR detected the virus in 40% of these patients.

Nucleoside analogs have been used for anti-viral therapy. For example, acyclovir and ganciclovir (see, Scheme 1 below) have been the mainstream therapy for infections by herpes viruses (e.g. herpes simplex virus (HSV), varicella zoster virus (VZV), Epstein-Barr virus (EPV) and cytomegalovirus (CMV)). These deoxyguanosine analogs are compounds that must be phosphorylated first by the viral thymidine kinase (V-TK) and then by cellular kinases to their triphosphate active form [Brigden & Whiteman, 1983]. These analogs exert their antiviral activity by inhibiting the viral DNA polymerase (pol) and terminating viral DNA synthesis.

Scheme 1

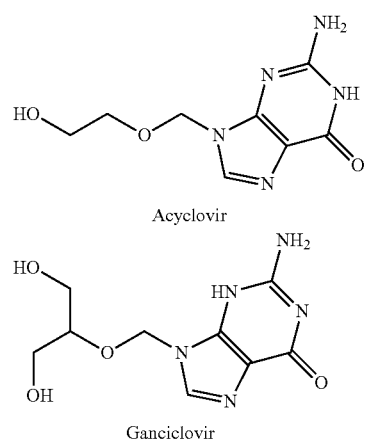

Acyclovir

Ganciclovir

Because acyclovir and ganciclovir are poor substrates for human monophosphatase kinase they have high selectivity and few side-effects, e.g., acyclovir has a selective activity which results in the inhibition of herpes virus replication at concentrations 300-3000-fold lower than those inhibiting mammalian cellular functions [Brigden & Whiteman, 1983]. Ganciclovir is a derivative of acyclovir with the addition of a hydroxymethylene, at the 3' carbon acyclic side-chain which gives increased activity, especially against HSV. Additional, other purinic and pyrimidinic antiviral agents with improved activity and oral bioavailability have been described [De Clerq & Field, 2006].

While due to the selectivity of these deoxyguanosine analogs these compounds are highly safe for humans, this selectivity renders these compounds lacking an anticancer activity per se.

However, these anti-viral nucleoside analogs may have an anticancer activity when combined with other compounds. Such combinations are being investigated for use in cancer therapy according to two approaches: suicide gene therapy and combination therapy of acyclovir with a histone deacetylase (HDAC) inhibitor.

Gene therapy strategy is based on the transfection of cancer cells with viral TK (V-TK) followed by treatment with pro-drugs such as acyclovir or ganciclovir, as described by Dachs et al., 2005. In this gene-directed enzyme prodrug therapy (GDEPT), the gene encoding the enzyme is delivered to tumor cells, followed by administration of ganciclovir, which is phosphorylated by V-TK to the monophosphate, which then undergoes a series of intracellular reactions resulting in the formation of the corresponding triphosphate. This triphosphate competes with deoxyguanosine triphosphate in DNA elongation during cell division, resulting in inhibition of DNA polymerase and single-strand breaks. The combination of enzyme and prodrug has specificity for rapidly dividing tumor cells invading normal quiescent tissue resulting in selective tumor cell-killing activity.

The second strategy focuses on lymphoproliferative disorders associated with Epstein-Barr virus (EBV) infections. Lymphoproliferative diseases associated with the EBV occur in immunocompromised patients as well as in other types of neoplasm e.g., oral and gastric cancer [Herrmann & Niedobitek, 2003; Perrine et al., 2007].

The lack of viral TK expression in EBV-positive tumors is caused by viral latency, which makes antiviral therapy alone ineffective as an antineoplastic therapy. The combination treatment strategy is based on using pharmacological induction of the latent viral TK gene and enzyme in tumor cells with a histone deacetylase (HDAC) inhibitor along with administration of ganciclovir. This treatment was developed as a combination of arginine butyrate and ganciclovir that was reported to be reasonably well-tolerated and seemed to have significant biological activity in vivo in EBV(+) lymphoid malignancies which are refractory to other regimens [Perrine et al., 2007].

U.S. Pat. No. 4,146,715 teaches purine derivatives, including amides and esters, as well as uses thereof as antiviral agents or in the preparation of antiviral agents.

WO 05/120577 teaches conjugates of a chemotherapeutic agent which are capable of releasing formaldehyde upon cleavage, and uses thereof.

SUMMARY OF THE INVENTION

As discussed herein, the inventors of the present invention have surprisingly found that compounds comprising at least one acyl moiety attached to a nucleoside analog exhibit potent anticancer activity.

According to an aspect of some embodiments of the invention there is provided a compound having Formula I:

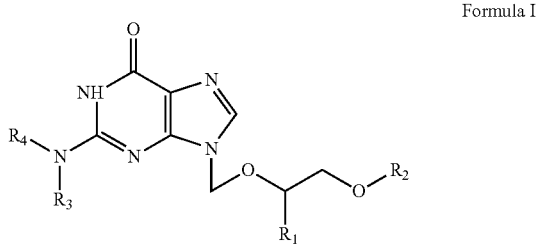

Formula I wherein:

$R_1$ is selected from the group consisting of H and —$CH_2OR_5$; and $R_2$, $R_3$, $R_4$ and $R_5$ are each independently hydrogen or an acyl moiety selected from the group consisting of butyryl, valproyl, 4-phenylbutyryl, cinnamoyl, phenylacetyl, 2-(4-isobutylphenyl)propionyl, 1-(butyryloxymethoxy)succinyl, 1-(valproyloxymethoxy)succinyl, 1-(4-phenylbutyryloxymethoxy)succinyl, 1-(cinnamoyloxymethoxy)succinyl, (phenylacetoxymethoxy)succinyl and 1-(2-(4-isobutylphenyl)propionyloxymethoxy)succinyl, provided that at least one of $R_2$, $R_3$ and $R_4$ is the acyl moiety.

The compound of claim 1, wherein $R_2$, $R_3$, $R_4$ and $R_5$ are each independently selected from the group consisting of H, butyryl, 4-phenylbutyryl, cinnamoyl and valproyl.

According to some embodiments, $R_1$ is H.

According to some embodiments, $R_4$ is H.

According to some embodiments, $R_2$ and $R_3$ are each butyryl.

According to some embodiments, $R_2$ and $R_3$ are each cinnamoyl.

According to some embodiments, $R_2$ is valproyl and $R_3$ is H.

According to some embodiments, $R_2$ is 4-phenylbutyryl and $R_3$ is H.

According to some embodiments, $R_3$ is valproyl and $R_2$ is H.

According to some embodiments, $R_2$ is 2-(4-isobutylphenyl)propionyl and $R_3$ is H.

According to some embodiments, $R_2$ is phenylacetyl and $R_3$ is H.

According to some embodiments, $R_2$ and $R_3$ are each valproyl.

According to an aspect of some embodiments of the invention, there is provided N-valproyl-9-(2-valproyloxy)ethoxymethylguanine.

According to an aspect of some embodiments of the invention there is provided a use of a compound described hereinabove in the manufacture of a medicament for the treatment of a proliferative disorder or disease.

According to an aspect of some embodiments of the invention there is provided a method of treating a proliferative disorder or disease, the method comprising administering to a subject in need thereof an effective amount of a compound described hereinabove.

According to an aspect of some embodiments of the invention there is provided a compound having Formula II:

A-X—B                          Formula II wherein:

X is a purinic or pyrimidinic nucleoside analog having at least one hydroxyl group and/or at least one amino group;

A is one or two acyl moieties attached to an amino group of the X or absent; and B is an acyl moiety attached to a hydroxyl group of the X or absent;

each of the acyl moieties, if present, being independently selected from the group consisting of a —C(=$Y_1$)—Ra group and a —C(=$Y_2$)-L-C(=$Y_3$)—OCH$_2$OC(=$Y_4$)—Rb group, whereas:

Ra and Rb are each independently selected from the group consisting of a substituted or non-substituted alkyl having 1-20 carbon atoms and a substituted or non-substituted alkenyl having 2-20 carbon atoms;

L is selected from the group consisting of a substituted or non-substituted alkyl having 1-4 carbon atoms and a substituted or non-substituted alkenyl having 2-4 carbon atoms; and $Y_1$, $Y_2$, $Y_3$ and $Y_4$ are each independently O or S, provided that at least one of A and B is not absent, with the proviso that when A is a purinic nucleoside analog, at least one of the acyl moieties is the —C(=$Y_2$)-L-C(=$Y_3$)—OCH$_2$C(=$Y_4$)—Rb group.

According to an aspect of embodiments of the invention there is provided a use of the compound having the Formula:

A-X—B                          Formula III wherein:

X is a purinic or pyrimidinic nucleoside analog having at least one hydroxyl group and/or at least one amino group;

A is one or two acyl moieties attached to an amino group of the X or absent; and B is an acyl moiety attached to a hydroxyl group of the X or absent;

each of the acyl moieties, if present, being independently selected from the group consisting of a —C(=$Y_1$)—Ra group and a —C(=$Y_2$)-L-C(=$Y_3$)—OCH$_2$C(=$Y_4$)—Rb group, whereas Ra and Rb are each independently selected from the group consisting of a substituted or non-substituted alkyl having 1-20 carbon atoms and a substituted or non-substituted alkenyl having 2-20 carbon atoms, L is selected from the group consisting of a substituted or non-substituted alkyl having 1-4 carbon atoms and a substituted or non-substituted alkenyl having 2-4 carbon atoms, and $Y_1$, $Y_2$, $Y_3$ and $Y_4$ are each independently O or S, provided that at least one of A and B is not absent, in the manufacture of a medicament for the treatment of a proliferative disorder or disease.

According to an aspect of embodiments of the invention there is provided a method of treating a proliferative disorder or disease, the method comprising administering to a subject in need thereof an effective amount of a compound having the formula:

A-X—B      Formula III wherein:

X is a purinic or pyrimidinic nucleoside analog having at least one hydroxyl group and/or at least one amino group;

A is one or two acyl moieties attached to an amino group of the X or absent; and B is an acyl moiety attached to a hydroxyl group of the X or absent;

each of the acyl moieties, if present, being independently selected from the group consisting of a —C(=$Y_1$)—Ra group and a —C(=$Y_2$)-L-C(=$Y_3$)—OCH$_2$C(=$Y_4$)—Rb group, whereas Ra and Rb are each independently selected from the group consisting of a substituted or non-substituted alkyl having 1-20 carbon atoms and a substituted or non-substituted alkenyl having 2-20 carbon atoms, L is selected from the group consisting of a substituted or non-substituted alkyl having 1-4 carbon atoms and a substituted or non-substituted alkenyl having 2-4 carbon atoms, and $Y_1$, $Y_2$, $Y_3$ and $Y_4$ are each independently O or S, provided that at least one of A and B is not absent.

According to some embodiments, each of the acyl moieties is independently derived from a carboxylic acid capable of inhibiting histone deacetylase.

According to some embodiments, the carboxylic acid capable of inhibiting histone deacetylase is selected from the group consisting of butyric acid, 4-phenylbutyric acid, valproic acid, phenylacetic acid, 2-(4-isobutylphenyl)propionic acid and cinnamic acid.

According to some embodiments, Ra and Rb are each independently selected from the group consisting of propyl, 3-phenylpropyl, 4-heptyl, phenylmethyl, 1-(4-isobutylphenyl)ethyl and styryl.

According to some embodiments, at least one of the acyl moieties is valproyl.

According to some embodiments, B and at least one acyl moiety in A are both valproyl.

According to some embodiments, at least one of the acyl moieties is butyryl.

According to some embodiments, B and at least one acyl moiety in A are both butyryl.

According to some embodiments, the nucleoside analog has an antiviral activity triggered by viral thymidine kinase (V-TK).

According to some embodiments, the nucleoside analog is selected from the group consisting of abacavir, acyclovir, adefovir, brivudine, cidofovir, clevudine, didanosine, edoxudine, emtricitabine, entecavir, famciclovir, floxuridine, ganciclovir, idoxuridine, inosine pranobex, lamivudine, penciclovir, sorivudine, stavudine, ribavirin, telbivudine, tenofovir, trifluridine, valacyclovir, valganciclovir, vidarabine, zalcitabine, and zidovudine.

According to some embodiments, the nucleoside analog is selected from the group consisting of acyclovir and ganciclovir.

According to some embodiments, B is —C(=$Y_1$)—Ra.

According to some embodiments, B is —C(=$Y_2$)-L-C(=$Y_3$)—OCH$_2$C(=$Y_4$)—Rb.

According to some embodiments, L is a non-substituted alkylene having the formula (CH$_2$)n, wherein n is an integer in the range of 1 to 4.

According to some embodiments, n is 2.

According to some embodiments, A is —C(=$Y_1$)—Ra.

According to an aspect of embodiments of the invention there is provided a pharmaceutical composition comprising a compound described hereinabove and a pharmaceutically acceptable carrier.

According to some embodiments, the pharmaceutical composition is packaged in packaging material and identified in print, in or on the packaging material, for use in the treatment of a proliferative disorder or disease.

According to some embodiments, the proliferative disorder or disease is characterized as being caused by a virus.

According to some embodiments, the virus is Epstein-Barr virus.

According to some embodiments, the proliferative disease or disorder is cancer.

According to some embodiments, the cancer is selected from the group consisting of sarcoma, leukemia, carcinoma and adenocarcinoma.

According to some embodiments, the cancer is selected from the group consisting of breast cancer, hepatoma, liver cancer, pancreatic carcinoma, oesophageal carcinoma, bladder cancer, gastrointestinal cancer, T-cell leukemia, Kaposi's sarcoma, squamous cell carcinoma (SCC) of the skin, pulmonary carcinoma, ovarian cancer, skin cancer, prostate cancer, Ewing's sarcoma and gastric cancer.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a scheme presenting a general assay for acyclovir phosphorylation by a kinase (e.g. herpes simplex virus thymidine kinase) wherein phosphorylation of acyclovir results in a decrease in the concentration of NADH, which may be measured by fluorometry.

Figure 2A:
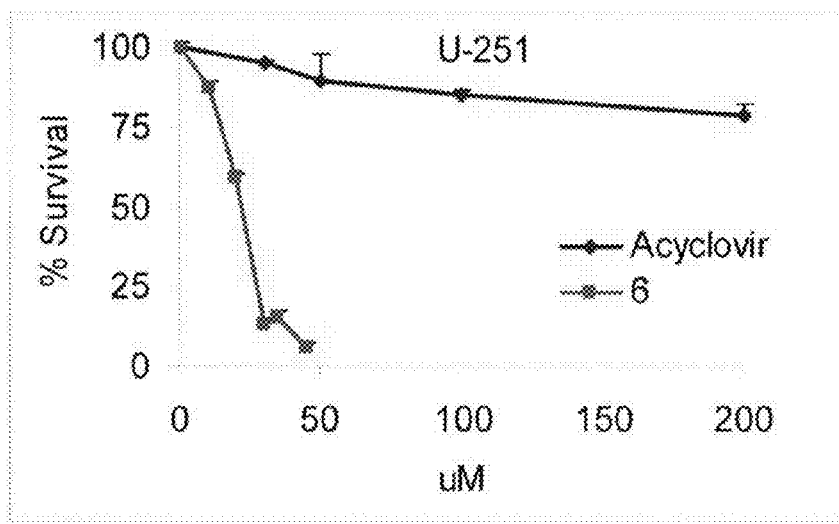
Figure 2B:
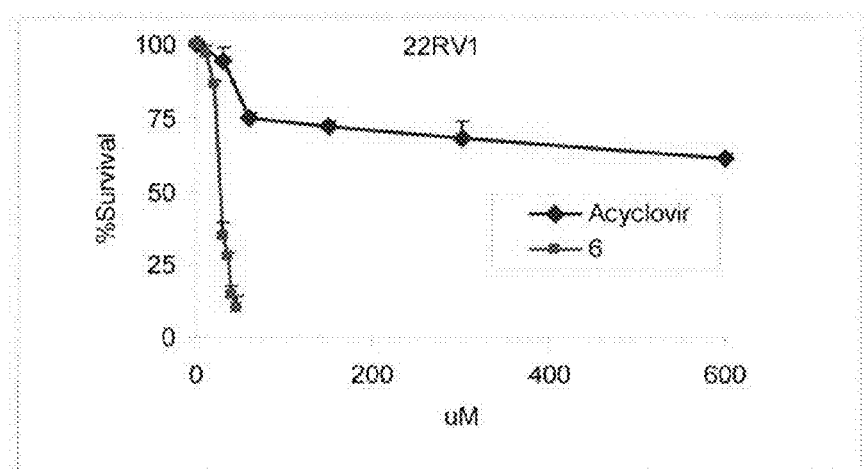

FIGS. 2a-b present comparative plots demonstrating the increased toxicity of Compound 6 as described herein towards U-251 cells (FIG. 2a) and 22RV1 cells (FIG. 2b) in comparison with acyclovir, as determined by a Hoechst viability assay; data represent the average of values obtained from at least 3 experiments, each experiment being performed in triplicate.

Figure 3A:
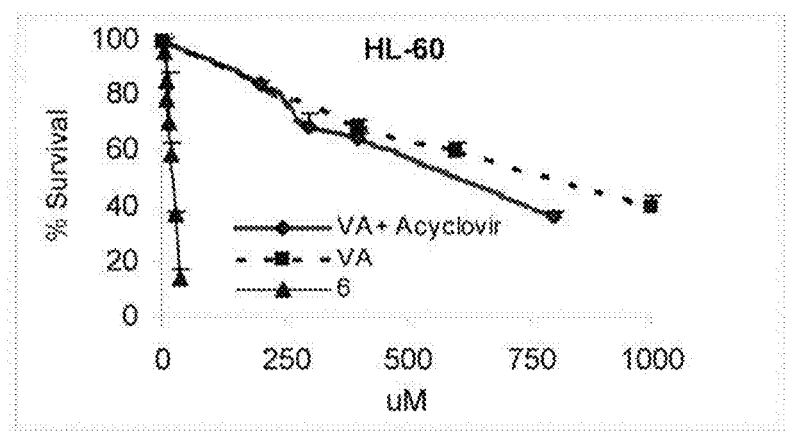
Figure 3B:
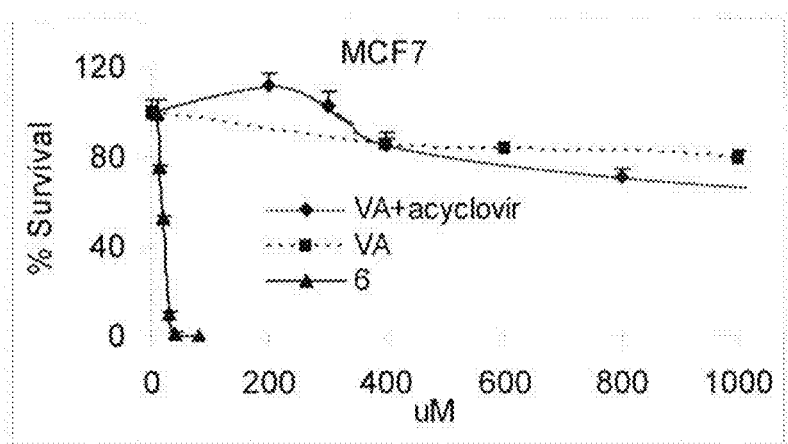
Figure 3C:
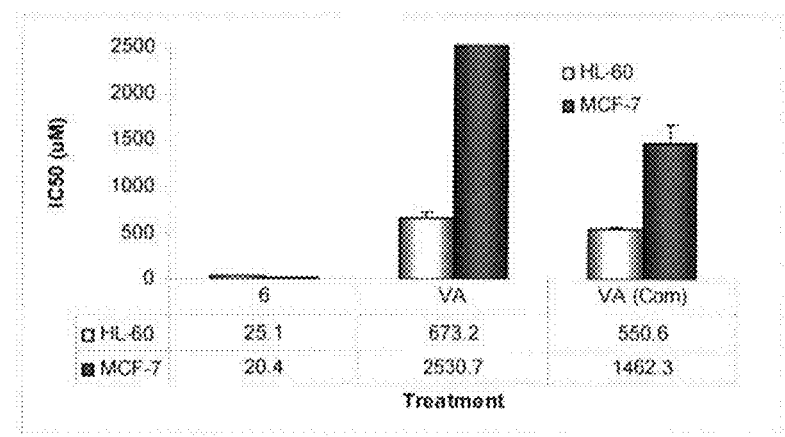

FIGS. 3a-c present comparative plots (FIGS. 3a and 3b) and a bar graph (FIG. 3c) demonstrating the increased toxicity of Compound 6 as described herein towards HL-60 cells, as determined by an MTT assay (FIG. 3a), and towards MCF-7 cells, as determined by a Hoechst assay (FIG. 3b), in comparison with valproic acid (VA) and a 2:1 mixture of valproic acid and acyclovir, as well as the corresponding $IC_{50}$ values for each compound in HL-60 and MCF-7 cells (FIG. 3c).

Figure 4A:
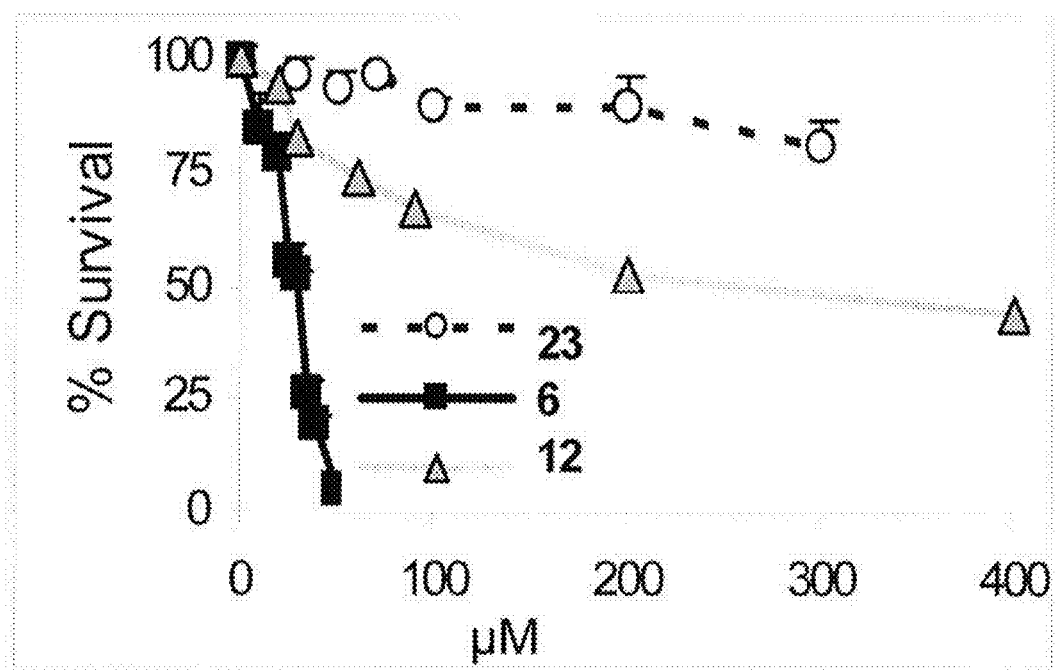
Figure 4B:
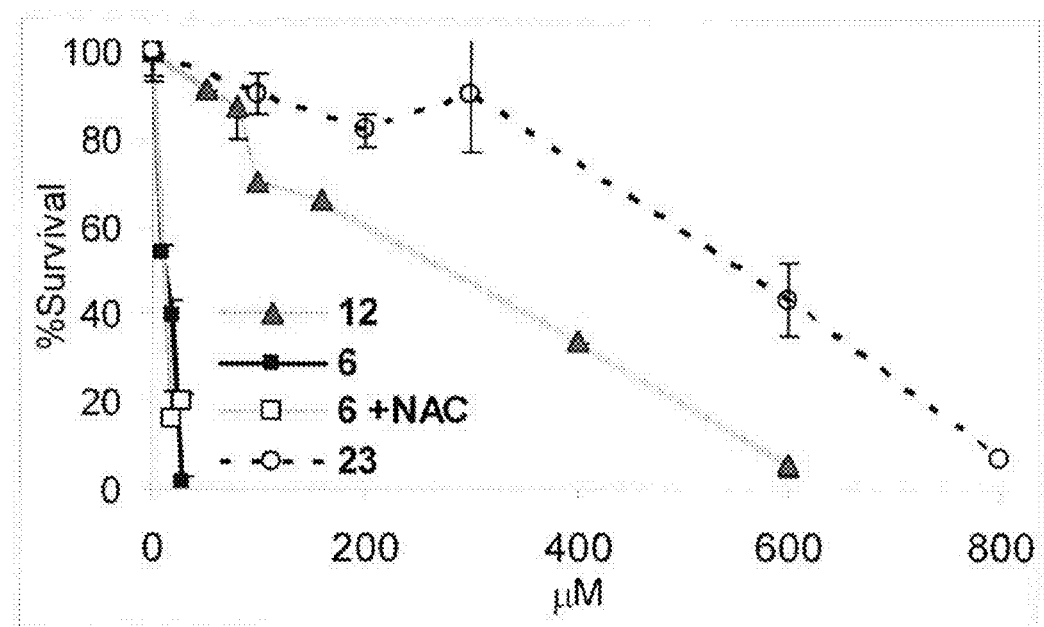

FIGS. 4a-b present comparative plots demonstrating the relative toxicities of Compounds 6, 12 and 23 towards U-251 cells (FIG. 4a) and 22RV1 cells (FIG. 4b), and the lack of an effect of 400 μM N-acetylcysteine (NAC) on the toxicity of Compound 6 (FIG. 4b), as determined by a Hoechst viability assay.

Figure 5:
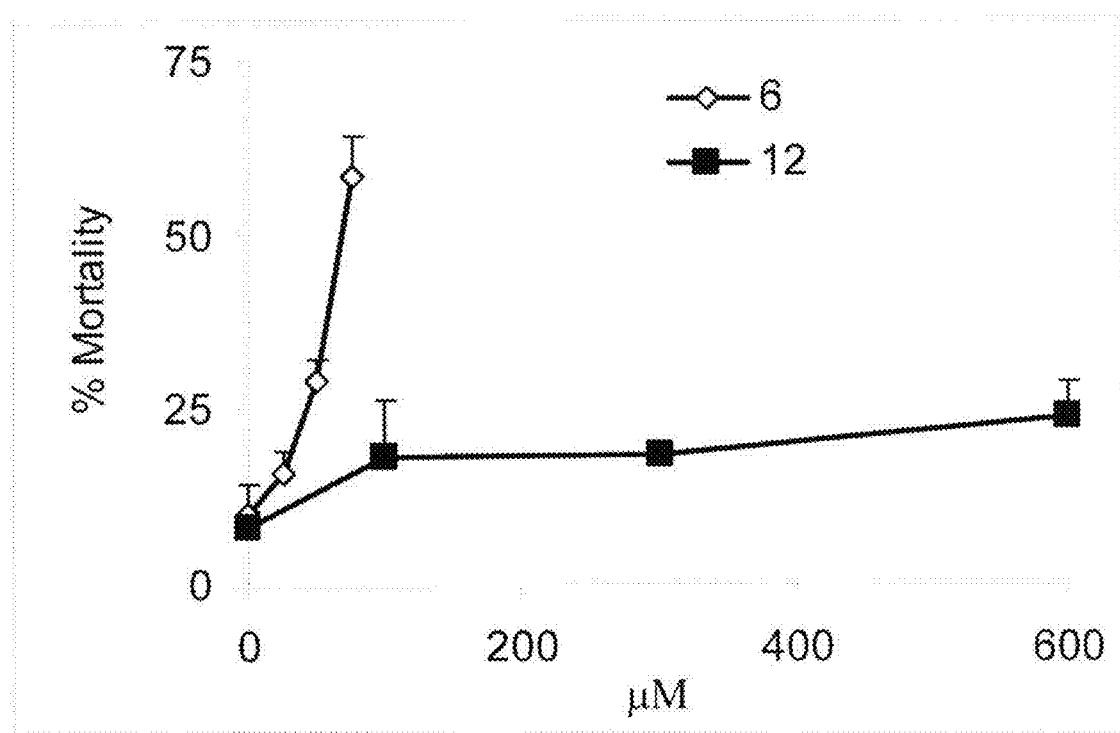

FIG. 5 is a graph demonstrating the relative toxicities of Compounds 6 and 12 towards U-251 cells, as determined by fluorescence-activated cell sorting (FACS) analysis of cells stained with annexin V-fluorescein isothiocyanate and propidium iodide.

Figure 6:
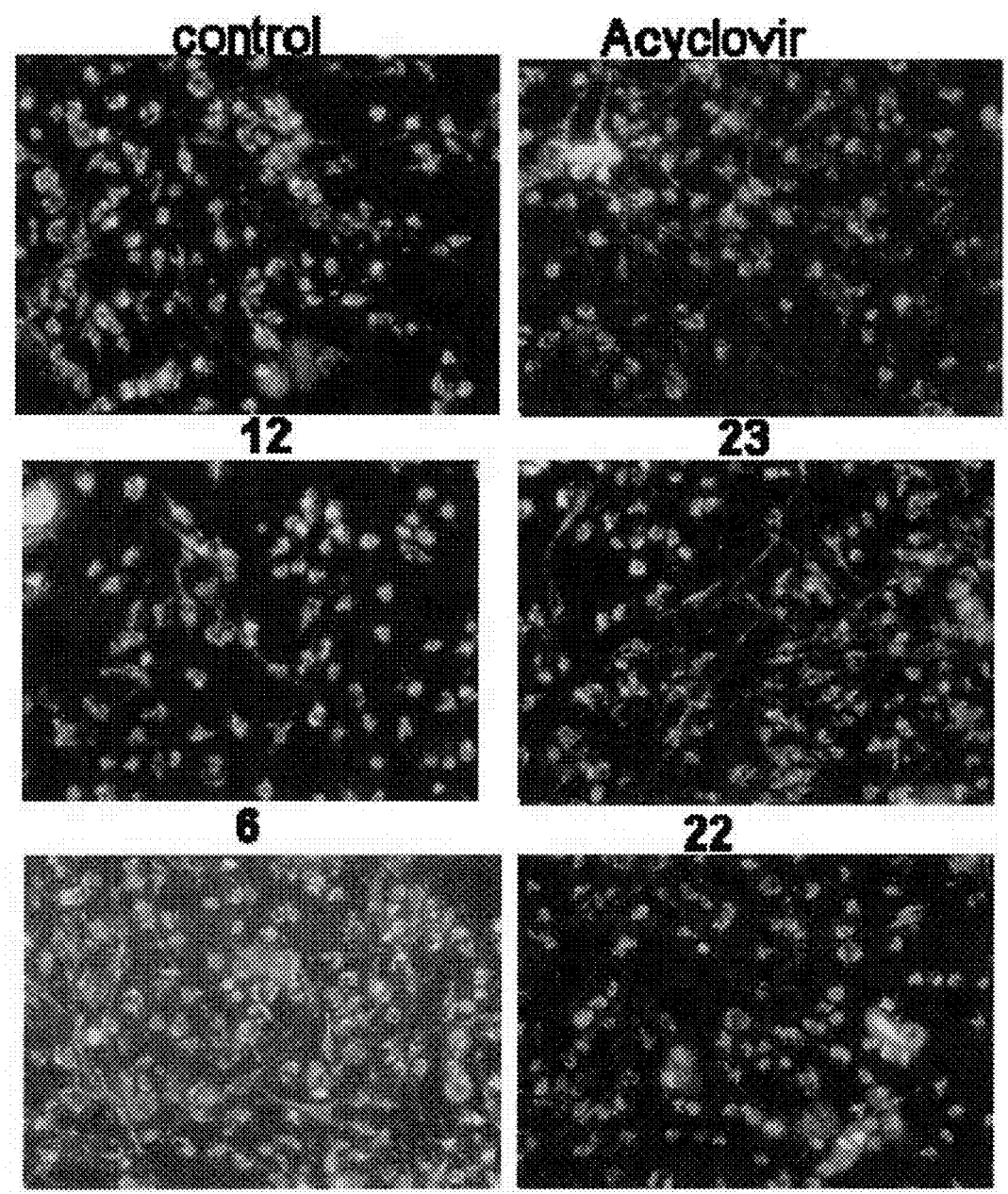

FIG. 6 presents photographs demonstrating the effects of 24 hour treatment with acyclovir and Compounds 6, 12, 22 and 23 (60 μM) on mitochondrial membrane potential in U-251 cells; green fluorescence indicates low membrane potential, red fluorescence indicates normal membrane potential (magnification ×200).

Figure 7:
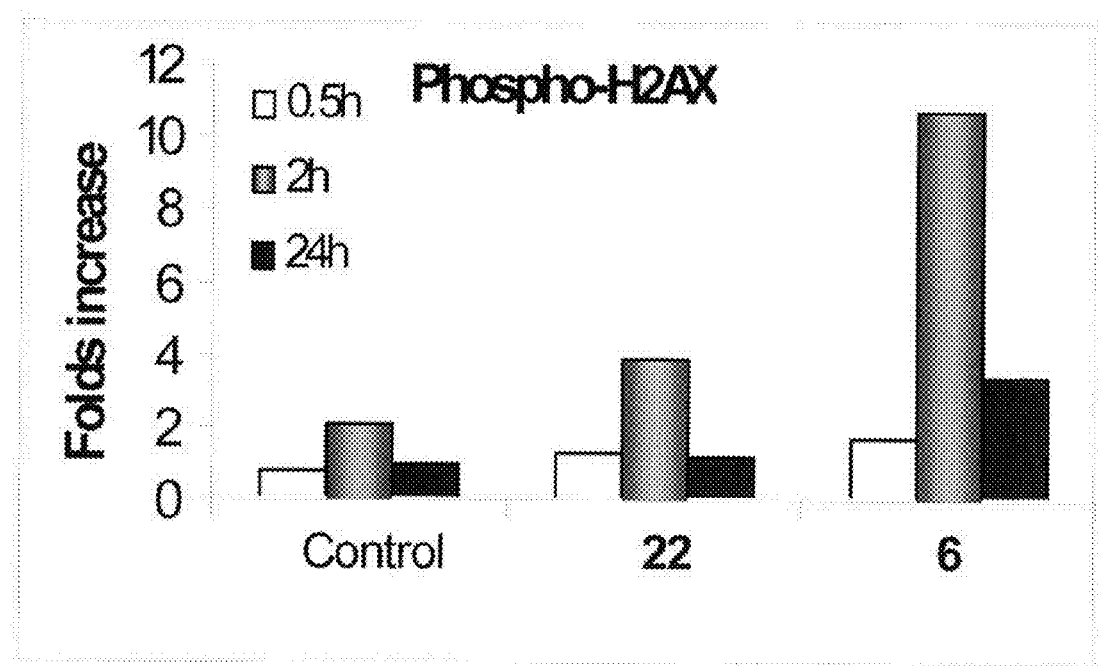

FIG. 7 is a bar graph demonstrating induction of H2AX phosphorylation by Compounds 6 and 22 (60 μM) in U-251 cells treated for 0.5, 2 or 24 hours, as determined by Western blot.

Figure 8:
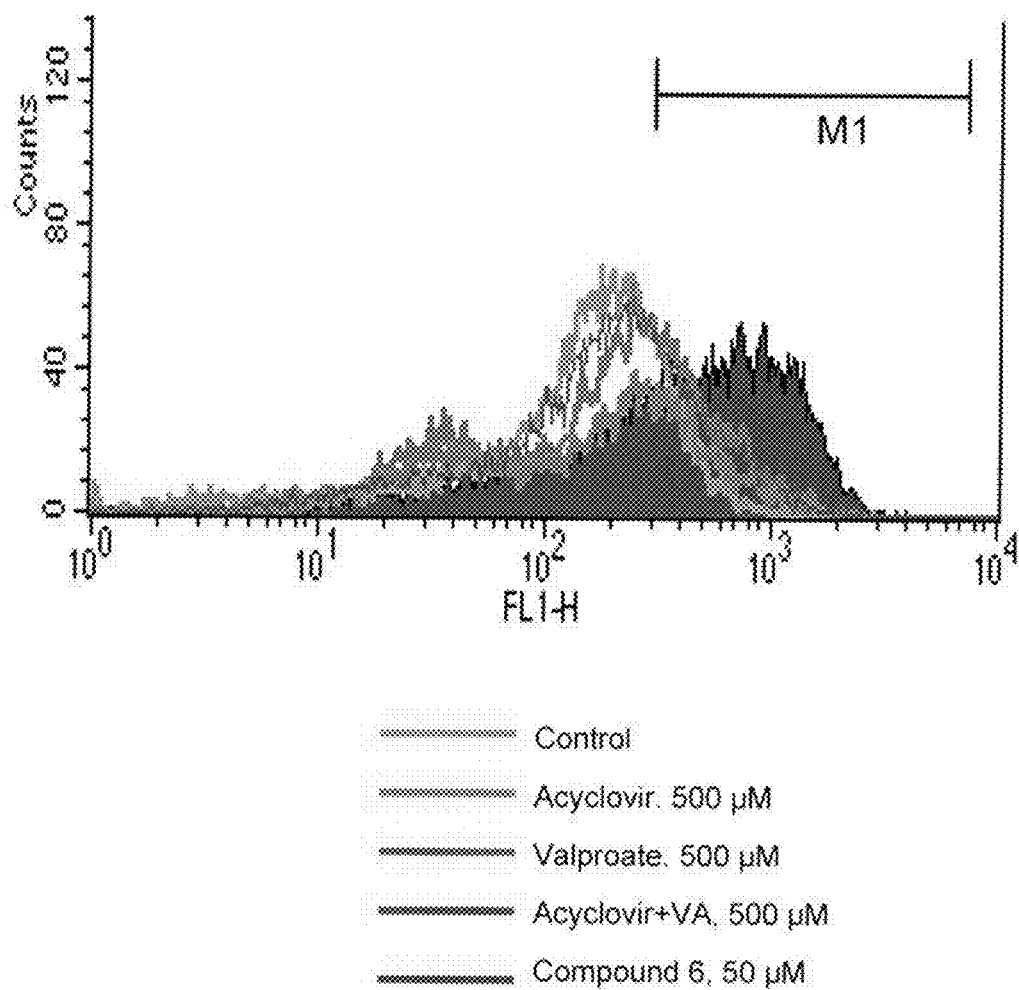

FIG. 8 is a histogram demonstrating that Compound 6, and not acyclovir or valproic acid (VA), increases oxidation in U-251 cells, as determined by FACS analysis following a 2 hour treatment of cells stained with dichlorodihydrofluorescein diacetate.

Figure 9:
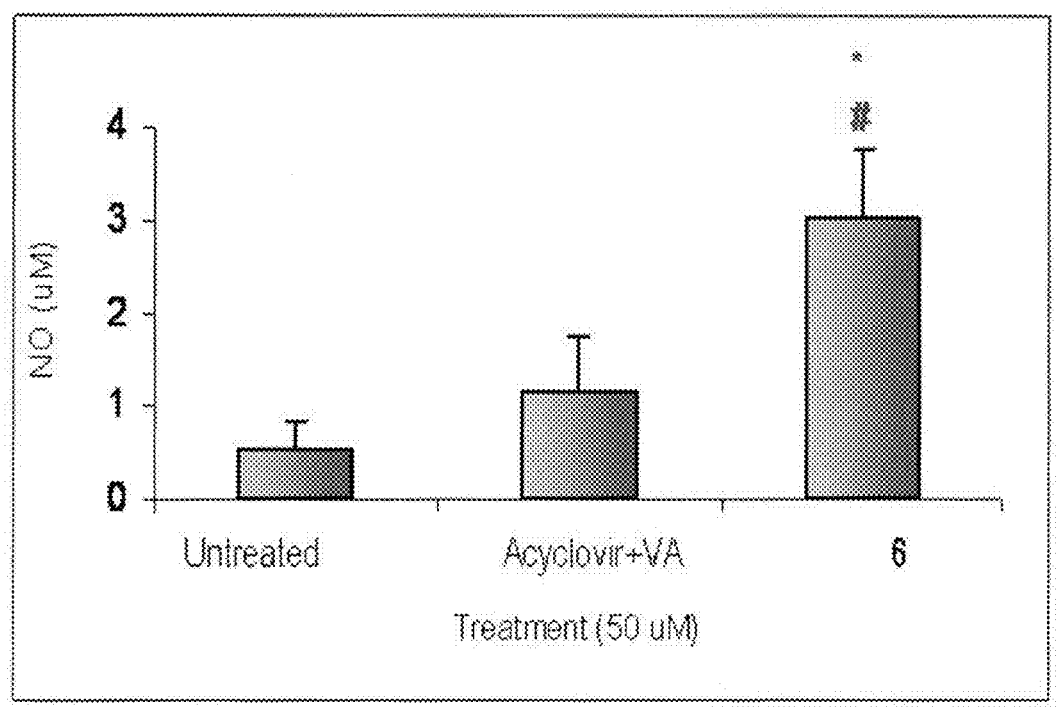

FIG. 9 is a bar graph demonstrating the induction of nitric oxide production in U-251 cells by 50 μM of Compound 6 and 50 μM acyclovir+50 μM valproic acid during a 1 hour treatment; data represent 12 samples for each group; * denotes significantly higher than untreated group ($p<0.05$); # denotes significantly higher than acyclovir+valproic acid group ($p<0.05$).

Figure 10:
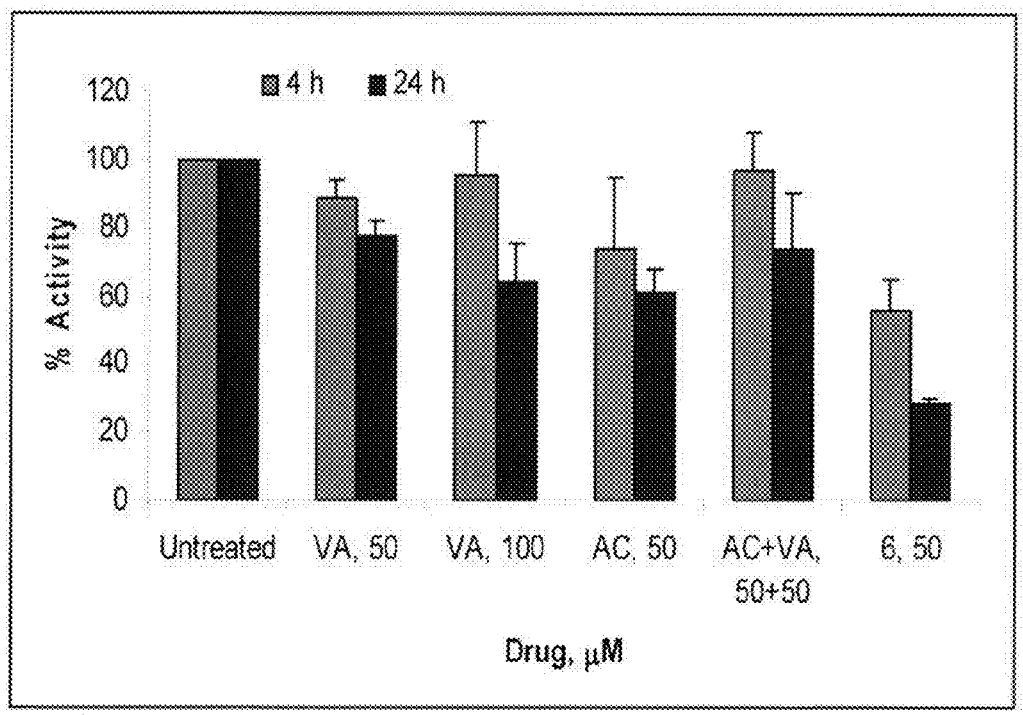

FIG. 10 is a bar graph demonstrating the proteasome activity in U-251 cells treated for 4 or 24 hours with valproic acid (VA), acyclovir (AC) and Compound 6 (50 or 100 μM).

Figure 11:
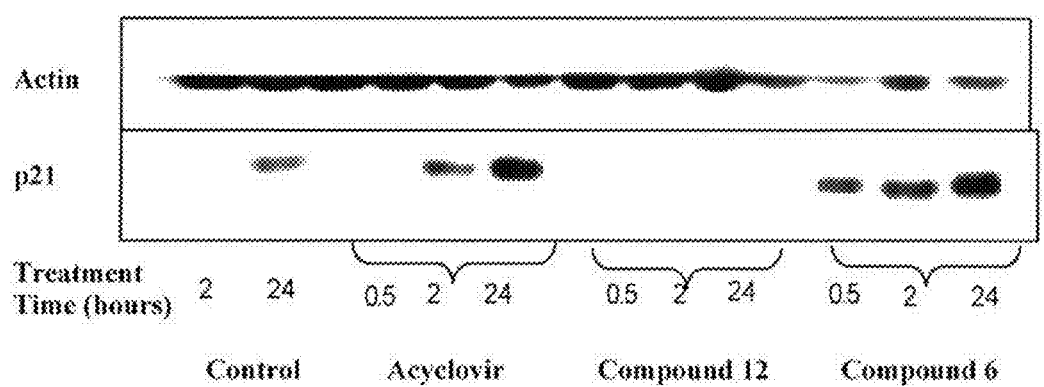

FIG. 11 presents a photograph of a Western blot demonstrating the effects of acyclovir and Compounds 6 and 12 on expression of cyclin-dependent kinase p21 in U-251 cells (actin expression serves as a control).

Figure 12:
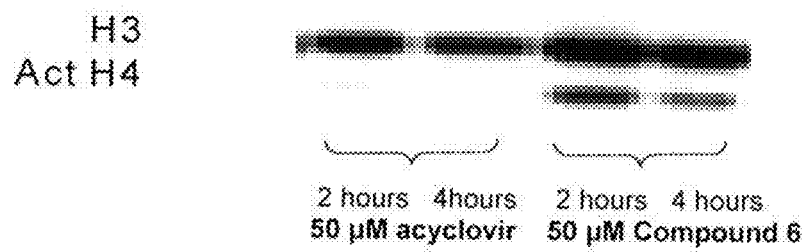

FIG. 12 is a photograph presenting a Western blot indicating that Compound 6, increases levels of acetylated histone H4 (Act H4) in U-251 cells (histone H3 expression serves as a control).

Figure 13A:
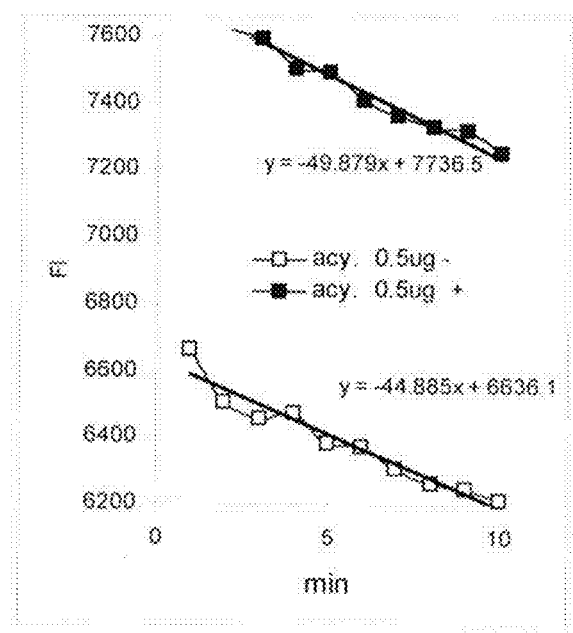
Figure 13B:
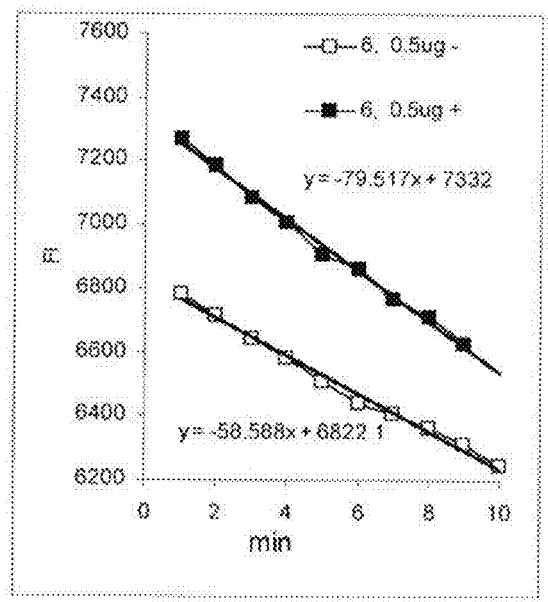

FIGS. 13a-b present comparative plots demonstrating the effects of incubation for 24 hours with 40 μM acyclovir (FIG. 13a) and Compound 6 (FIG. 13b) on the rate of acyclovir phosphorylation in 4T1 cells; y-axis represents NADH fluorescence (arbitrary units).

Figure 14:
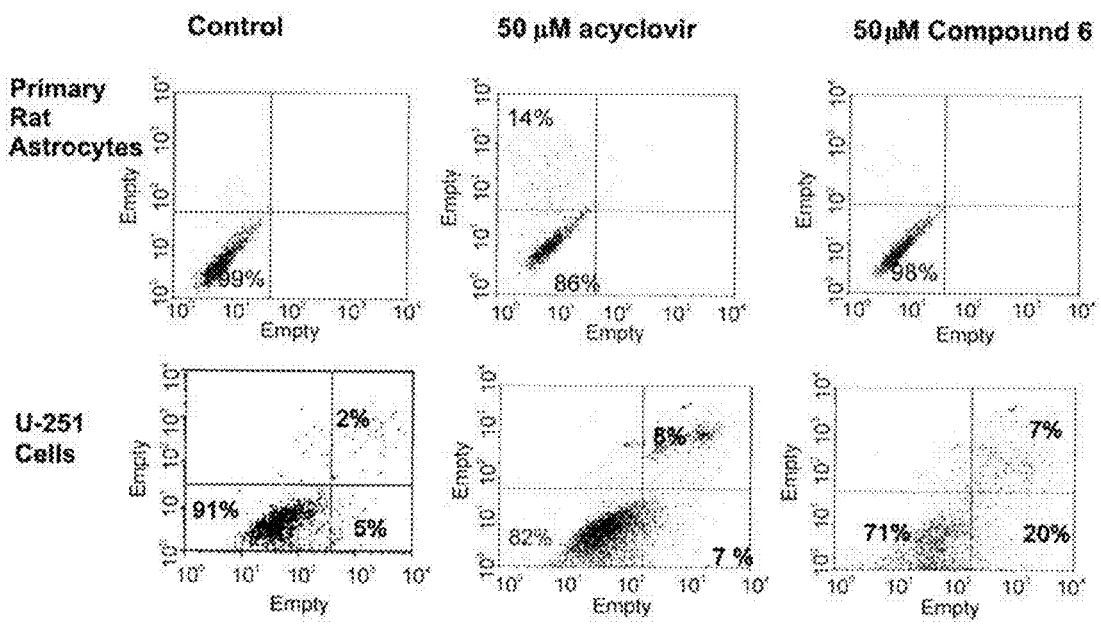

FIG. 14 presents plots demonstrating the effects of incubation for 24 hours with acyclovir and Compound 6 (50 μM) on the viability of primary rat astrocytes and U-251 cells, as determined by FACS analysis of cells stained with annexin V-fluorescein isothiocyanate and propidium iodide (y-axis represents propidium iodide fluorescence, x-axis represents fluorescein isothiocyanate fluorescence).

Figure 15:
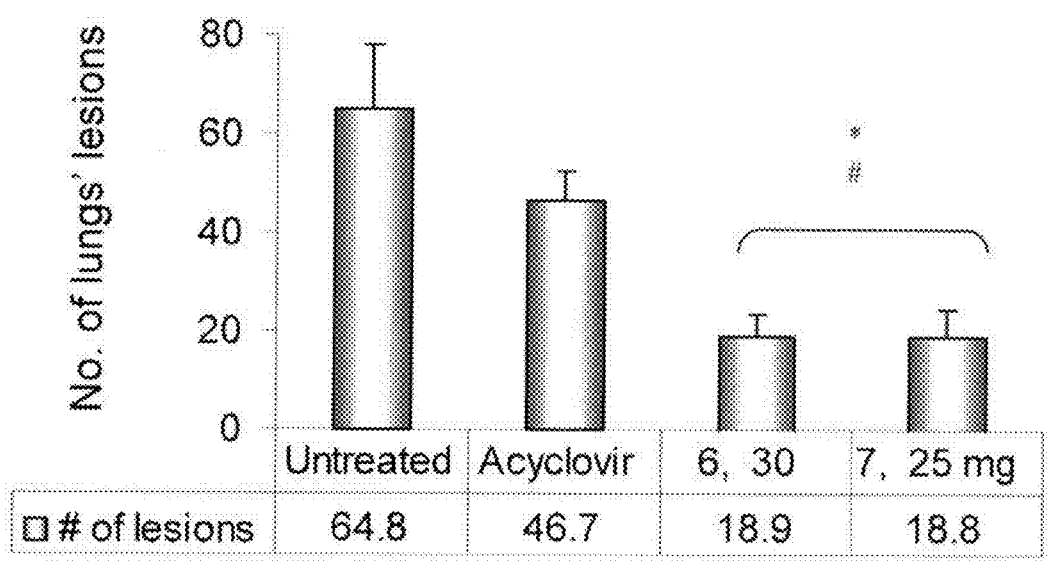

FIG. 15 is a bar graph demonstrating the reduction of the number of lung lesions by Compounds 6 (30 mg/kg) and 7 (25 mg/kg) in a murine Lewis lung carcinoma model (11 mice per group; oral (gavage) treatment 3 times per week; $p<0.02$ for both groups vs. acyclovir group (#) and untreated group (*)).

Figure 16A:
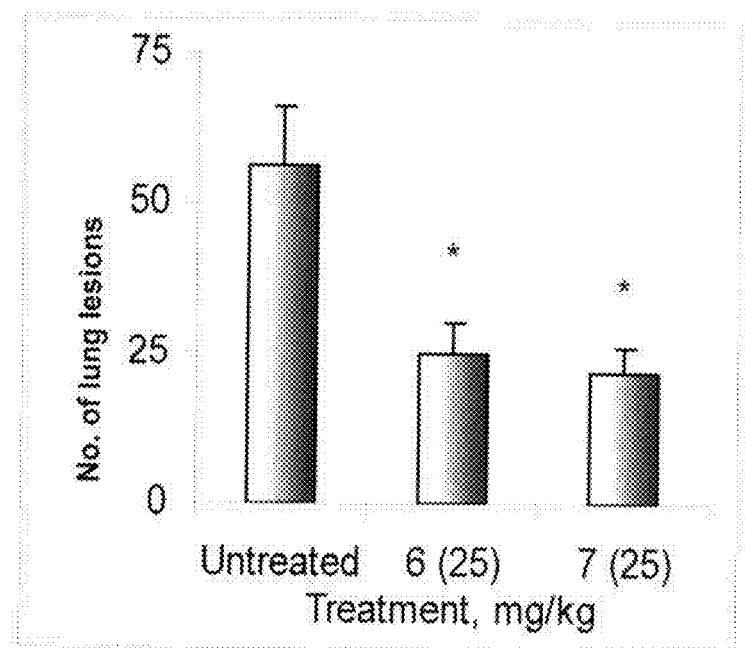
Figure 16B:
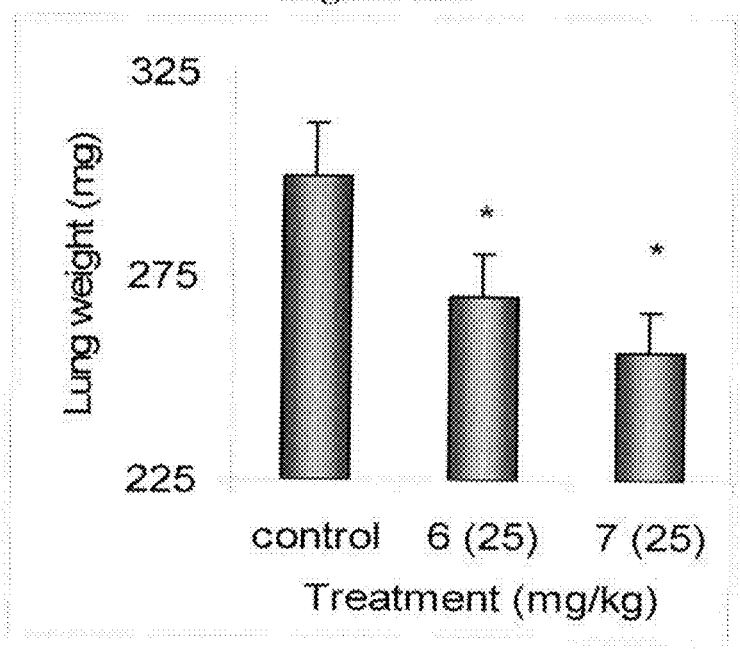

FIGS. 16a-b present bar graphs demonstrating the reduction of the number of metastases (FIG. 16a) and lung weight (FIG. 16b) by Compounds 6 and 7 in a murine 4T1 metastatic breast carcinoma model (10 mice per group; $p<0.05$ for both groups).

Figure 17A:
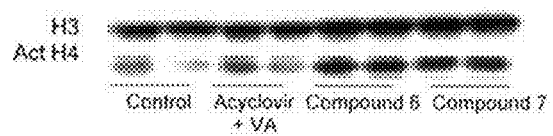
Figure 17B:
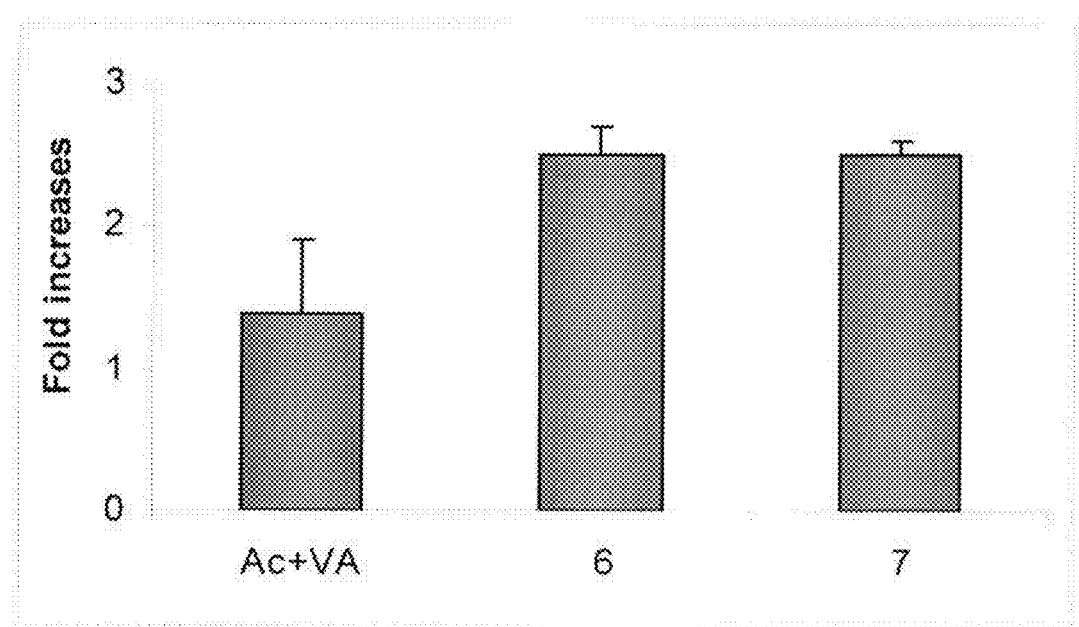

FIGS. 17a-b present a photograph of a Western blot (FIG. 17a) and a bar graph summarizing the results of the Western blot (FIG. 17b) demonstrating the increase in levels of acetylated histone H4 (Act H4) by acyclovir (AC)+valproic acid (VA) and Compounds 6 and 7 (100 mg/kg each) in 1 $cm^3$ murine 4T1 tumors 4 hours after treatment (histone H3 expression serves as a control).

Figure 18A:
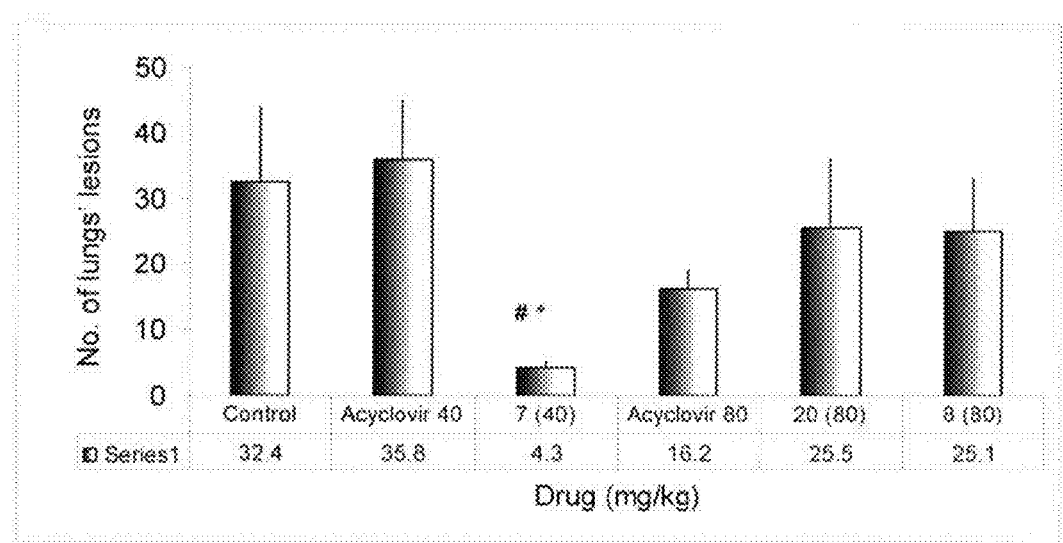
Figure 18B:
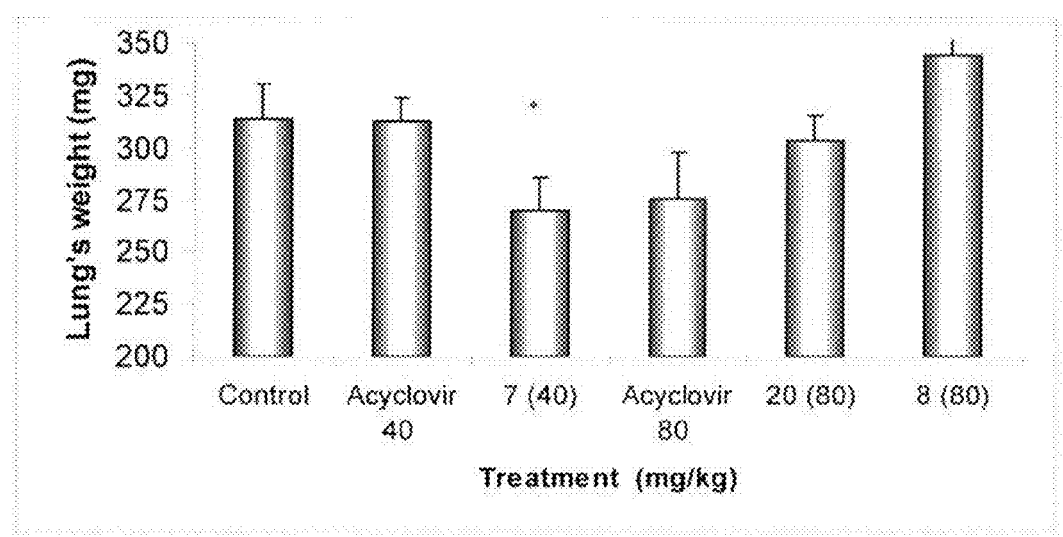

FIGS. 18a-b present bar graphs demonstrating the effects of acyclovir and Compounds 7, 8 and 20 (40 or 80 mg/kg) on the number of metastases (FIG. 18a) and lung weight (FIG. 18b) in a murine 4T1 metastatic breast carcinoma model (10 mice per group); only Compound 7 group exhibits significant reductions ($p<0.05$) vs. acyclovir group (#) and untreated group (*).

DESCRIPTION OF SPECIFIC EMBODIMENTS OF THE INVENTION

The present invention, in some embodiments thereof, relates to novel compounds, and more particularly, but not exclusively, to derivatives of nucleoside analogs which can be used in anti-cancer therapy.

The principles and operation of the compositions and methods according to some embodiments of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As is shown in the Examples section hereinbelow, while reducing the present invention to practice, it was shown, using a Hoechst viability assay, that exemplary acylated derivatives of nucleoside analogs kill cancer cells in vitro (see, for example, FIGS. 2-4). Moreover, the anticancer effect of exemplary acylated derivatives of nucleoside analogs was surprisingly shown to be considerably greater than the anticancer effects of a combination of the hydrolysis products (i.e., nucleoside analogs and carboxylic acids) of the acylated derivative (see, for example, FIG. 3). Exemplary acylated derivatives of nucleoside analogs were shown to increase apoptosis in cancer cells as determined by an annexin V assay (FIG. 5), measurement of mitochondrial membrane potential (see, for example, FIG. 6), and determination of phospho-H2AX levels (see, for example, FIG. 7). It was shown that exemplary acylated derivatives of nucleoside analogs increase levels of toxic reactive oxygen species and reactive nitrogen species in cancer cells (see, for example, FIGS. 8 and 9). Exemplary acylated derivatives of nucleoside analogs were also shown to block proteasome activity (see, for example, FIG. 10), and to induce cell cycle arrest (see, Table 2) in cancer cells.

Exemplary acylated derivatives of nucleoside analogs were shown to inhibit p21 expression (see, for example, FIG. 11) and to induce histone hyperacetylation (see, FIG. 12), both results indicating histone deacetylase inhibition. Exemplary acylated derivatives of nucleoside analogs were also shown to induce phosphorylation of acyclovir (see, FIG. 13).

The lethal effect of exemplary compounds was shown to be selective towards cancer cells (see, FIG. 14). The compounds were shown to be nontoxic in in vivo assays.

Exemplary derivatives of nucleoside analogs were further shown to exhibit an anti-metastatic effect in vivo (see, for example, FIGS. 15 and 16), and to induce histone acetylation in tumor cells (see, for example, FIG. 17).

Furthermore, nucleoside analogs acylated with acyl moieties derived from carboxylic acids capable of inhibiting histone deacetylase (HDAC) were shown to exhibit more potent anticancer activity than nucleoside analogs acylated with other acyl moieties (see, FIG. 18). Thus, it has been shown, in both in vivo and in vitro studies, that acylated derivatives of nucleoside analogs exhibit anti-cancer properties. It has been further shown that acylated derivatives of nucleoside analogs inhibit histone deacetylase.

The data presented herein demonstrate the efficacy of acylated derivatives of nucleoside analogs in treating proliferative diseases and disorders such as cancer.

As further described in the Examples section hereinbelow, novel exemplary acylated derivatives of nucleoside analogs, which may be useful for treating proliferative diseases and disorders, have been synthesized.

Hence, according to one aspect of embodiments of the present invention, there is provided a compound having Formula II:

A-X—B                    Formula II wherein:

X is a purinic or pyrimidinic nucleoside analog having at least one hydroxyl group and/or at least one amino group;

A is one or two acyl moieties attached to an amino group of the nucleoside analog or absent; and B is an acyl moiety attached to a hydroxyl group of the nucleoside analog or absent;

each of said acyl moieties, if present, being independently selected from the group consisting of a —C(=$Y_1$)—Ra group and a —C(=$Y_2$)-L-C(=$Y_3$)—OCH$_2$C(=$Y_4$)—Rb group, whereas Ra and Rb are each independently selected from the group consisting of a substituted or non-substituted alkyl having 1-20 carbon atoms and a substituted or non-substituted alkenyl having 2-20 carbon atoms, L is selected from the group consisting of a substituted or non-substituted alkyl having 1-4 carbon atoms and a substituted or non-substituted alkenyl having 2-4 carbon atoms and $Y_1$, $Y_2$, $Y_3$ and $Y_4$ are each independently O or S, provided that at least one of A and B is not absent.

As used herein, the phrase "nucleoside analog" encompasses any compound having a molecular structure similar to a nucleoside (e.g., adenosine, guanosine, thymidine and cytidine, and deoxy derivatives thereof) and/or a nucleic base (e.g., adenine, guanine, thymine and cytosine). The term "analog" indicates that the compound is capable of interacting (e.g., as a substrate and/or inhibitor) with an enzyme for which a nucleoside and/or nucleic base is a natural substrate and/or inhibitor.

As used herein, the term "pyrimidinic" refers to nucleic bases (as well as to the corresponding nucleosides) having a pyrimidine backbone (e.g., thymine and cytosine), whereas the term "purinic" refers to nucleic bases (as well as to the corresponding nucleosides) having a purine backbone (e.g., adenine and guanine).

Exemplary nucleoside analogs suitable for use in the context of the present invention include, without limitation, abacavir, acyclovir, adefovir, brivudine, cidofovir, clevudine, didanosine, edoxudine, emtricitabine, entecavir, famciclovir, floxuridine, ganciclovir, idoxuridine, inosine pranobex, lamivudine, penciclovir, sorivudine, stavudine, ribavirin, telbivudine, tenofovir, trifluridine, valacyclovir, valganciclovir, vidarabine, zalcitabine, and zidovudine. Abacavir, acyclovir, adefovir, didanosine, entecavir, famciclovir, ganciclovir, inosine pranobex, penciclovir, tenofovir, valacyclovir, valganciclovir and vidarabine are purinic nucleoside analogs.

According to some embodiments of the present invention, the nucleoside analog has an antiviral activity.

In one embodiment, the nucleoside analog has an antiviral activity which is triggered by viral thymidine kinase (V-TK). As discussed hereinabove, triggering by V-TK results in a selective nucleoside analog. The nucleoside analog is converted into an active, phosphorylated form in cells having V-TK (i.e., cells infected with a virus) while remaining in the original inactive, non-phosphorylated form in other cells. By remaining in an inactive form in non-infected cells, side effects caused by damage to non-infected cells are reduced considerably.

In one embodiment, the nucleoside analog is acyclovir.

In another embodiment, the nucleoside analog is ganciclovir.

The nucleoside analogs described herein have one or more hydroxy and/or amino substituents, whereby at least one of these substituents is acylated.

The terms "hydroxy" and "hydroxyl", as used herein, describe a —OH group.

As used herein, the terms "amino" and "amine" describe both a —NR'— linking group and a —NR'R" end group, wherein R' and R" are each independently selected from the group consisting of hydrogen, alkyl, cycloalkyl, heteroalicyclic, aryl and heteroaryl, as these terms are defined hereinbelow.

An amino group can be a primary amine, where both R' and R" are hydrogen, a secondary amine, where R' is hydrogen and R" is alkyl, cycloalkyl, heteroalicyclic, aryl or heteroaryl, or a tertiary amine, where each of R' and R" is independently alkyl, cycloalkyl, heteroalicyclic, aryl or heteroaryl. However, in cases where an acyl moiety is attached to an amino group, as described hereinabove, the amino group is a primary amine, to which one or two acyl moieties may be attached, or a secondary amine, to which one acyl moiety may be attached.

When A is absent, the amino group of the nucleoside analog is —NR'R" as defined herein. Similarly, when B is absent, the hydroxyl group of the nucleoside analog is —OH as defined.

The phrase "acyl moiety", as used herein, describes a moiety having a structure —C(=O)—R* (acyl group) or —C(=S)—R* (thioacyl group), where R* may comprise one or more of any chemical group described herein.

For the sake of simplicity and brevity, herein throughout the phrase "acyl moiety" is used to describe both an acyl moiety having an acyl group and an acyl moiety having a thioacyl group, except where specifically indicated otherwise.

When A is one acyl moiety attached to an amino group of the nucleoside analog X, the acyl moiety is attached to X so as to form an amide (or thioamides) linking group, as defined herein. When A is two acyl moieties attached to an amino group of the nucleoside analog X, the acyl moieties are attached to X so as to form an imide (or thioimide) linking group, as defined herein.

In one embodiment of the present invention, A stands for one acyl moiety.

B is an acyl moiety attached to a hydroxy substituent of the nucleoside analog X, so as to form an ester (or thioester) linking group, as defined herein.

The term "amide" describes a —C(=O)NR'— linking group, a —C(=O)NR'R" end group (also referred to herein as "C-amide"), and a —NR'C(=O)R" end group (also referred to herein as "N-amide"), where R' and R" are as defined herein.

The term "thioamide" describes a —C(=S)NR'— linking group, a —C(=S)NR'R" end group (also referred to herein as "C-thioamide"), and a —NR'C(=S)R" end group (also referred to herein as "N-thioamide"), where R' and R" are as defined herein.

Herein throughout, the phrase "end group" describes a group (a substituent) that is attached to another moiety in the compound via one atom thereof.

The phrase "linking group" describes a group (a substituent) that is attached to at least one other moiety in the compound via two or more atoms thereof.

The term "imide" describes a —C(=O)N(C(=O)R')— linking group, a —N((C=O)R')C(=O)R" end group and a —C(=O)N(C(=O)R')R" end group, where R' and R" are as defined herein.

The term "thioimide" describes a —C(=S)N(C(=S)R')— linking group, a —N((C=S)R')C(=S)R" end group and a —C(=S)N(C(=S)R')R" end group, where R' and R" are as defined herein.

The term "carboxylate" describes a —C(=O)O— linking group, a —C(=O)OR' end group (also referred to herein as "C-carboxylate") and a —OC(=O)R' (also referred to herein as "O-carboxylate"), where R' is as defined herein.

The term "ester" describes a carboxylate group, where R' is alkyl, cycloalkyl, heteroalicyclic, aryl or heteroaryl.

The term "thiocarboxylate" describes a —C(=S)O— linking group, a —C(=S)OR' end group (also referred to herein as "C-thiocarboxylate") and a —OC(=S)R' (also referred to herein as "O-thiocarboxylate"), where R' is as defined herein.

The term "thioester" describes a thiocarboxylate group, where R' is alkyl, cycloalkyl, heteroalicyclic, aryl or heteroaryl.

It is to be appreciated that when X has more than one hydroxyl group and/or more than one amino group, more than one amide, imide and/or ester group may be present, linking a plurality of acyl moieties with X.

As shown in Formula II above, the acyl moiety is either a —C(=Y$_1$)—Ra group or a —C(=Y$_2$)-L-C(=Y$_3$)—OCH$_2$C(=Y$_4$)—Rb group, as defined herein. In exemplary embodiments of the present invention, each of Y$_1$, Y$_2$, Y$_3$ and Y$_4$ is O.

According to an embodiment of the present invention, at least one acyl moiety is valproyl. In exemplary compounds, B is valproyl, and at least one acyl moiety in A is valproyl.

According to another embodiment of the present invention, at least one acyl moiety is butyryl. In exemplary compounds, B is butyryl, and at least one acyl moiety in A is butyryl.

As described hereinabove, the nucleoside analog (X in Formula II) may have more than one hydroxyl and/or amino group. Thus, for example, the phrase "B is valproyl" describes a compound having at least one acyl moiety, each being valproyl, each attached to a hydroxyl group of X. Similarly, the phrase "at least one acyl moiety in A is valproyl" describes a compound having at least one amino group of X attached to one or two acyl moieties, each such amino group being attached to at least one valproyl.

According to an embodiment of the present invention, B is —C(=Y$_1$)—Ra and A is absent.

According to another I embodiment of the present invention, B is —C(=Y$_2$)-L-C(=Y$_3$)—OCH$_2$C(=Y$_4$)—Rb and A is absent. According to another embodiment of the present invention, A is —C(=Y$_1$)—Ra and B is absent.

According to another embodiment of the present invention, A and B are both a C(=Y$_1$)—Ra acyl moiety, whereby the Ra group in each acyl moiety can be the same or different.

In another embodiment, A is —C(=Y$_1$)—Ra and B is —C(=Y$_2$)-L-C(=Y$_3$)—OCH$_2$C(=Y$_4$)—Rb In another embodiment, A is two —C(=Y$_1$)—Ra acyl moieties, being the same or different and B is absent, a —C(=Y$_1$)—Ra acyl group or a —C(=Y$_2$)-L-C(=Y$_3$)—OCH$_2$C(=Y$_4$)—Rb acyl group.

In some embodiments of this aspect of the present invention, when A is a purinic nucleoside analog, at least one of said acyl moieties is a —C(=Y$_2$)-L-C(=Y$_3$)—OCH$_2$C(=Y$_4$)—Rb group, as defined herein.

A compound having Formula II and comprising, as B, a C(=Y$_1$)—Ra acyl moiety is susceptible to being cleaved by cellular esterases, and hence is expected to release Ra—C(=Y$_1$)OH. A compound having Formula II and comprising, as B, a —C(=Y$_2$)-L-C(=Y$_3$)—OCH$_2$C(=Y$_4$)—Rb acyl moiety is susceptible to being cleaved by cellular esterases so as to release Rb—C(=Y$_4$)OH, formaldehyde and a dicarboxylic acid (or a thiocarboxylic derivative thereof, i.e. wherein at least one C(=O) is replaced by C(=S)) having a formula HOC(=Y$_2$)-L-C(=Y$_3$)OH.

Similarly, an acyl moiety comprised by A is susceptible to being cleaved (e.g. by an amidase), although cleavage of amides is typically slower in vivo than cleavage of esters.

Without being bound by any particular theory, it is believed that the formaldehyde released from compound having a —C(=Y$_2$)-L-C(=Y$_3$)—OCH$_2$C(=Y$_4$)—Rb acyl moiety has an antiproliferative effect, as described in WO 05/120577, and hence increases the potency of the compound. It is noted, however, that in the compounds according to these embodiments, the formaldehyde-releasing group is not attached directly to the nucleoside analog.

According to some embodiments, L is a non-substituted alkylene having the formula (CH$_2$)n, wherein n is an integer in the range of 1 to 4. Optionally, L is (CH$_2$)$_2$, such that the dicarboxylic acid released upon cleavage is succinic acid or a thiocarboxylic derivative thereof.

Without being bound by any particular theory, it is believed that the released succinic acid (or a thiocarboxylic derivative thereof) increases the anti-proliferative effects of the above-mentioned compound. It is further believed that the anti-proliferative effect of succinic acid is mediated by inhibition of histone demethylase.

Ra—C(=O)OH is defined herein as a carboxylic acid from which a —C(=O)—Ra acyl moiety is derived, and both Rb—C(=O)OH and Rb—C(=O)OCH$_2$O-L-C(=O)OH are defined herein as carboxylic acids from which a —C(=O)-L-C(=O)—OCH$_2$C(=O)—Rb acyl moiety is derived.

As used herein, a carboxylic acid from which an acyl moiety is derived, encompasses a carboxylic acid that upon attachment to the hydroxy and/or amine group of the nucleoside analog described herein yields the acyl moiety, and/or a carboxylic acid that is released from the compounds described herein upon contacting cellular esterases or amidases, as described herein.

In one embodiment, the acyl moiety described herein is derived from a carboxylic acid that is capable of inhibiting histone deacetylase (also referred to herein as histone deacetylase inhibitor or HDAC).

Without being bound by any particular theory, it is believed that many proliferative disorders and diseases are caused, at least in part, by viruses, but have not been satisfactorily treated hitherto with antiviral therapy due to the inherent difficulties caused by viral latency. Histone deacetylase inhibitors are believed to reduce viral latency, and have also been reported to have anti-proliferative effects. A compound having both an antiviral moiety and a moiety derived from a compound (e.g., a carboxylic acid) capable of inhibiting histone deacetylase exhibits a synergistic effect between the two moieties, so as to more effectively treat a proliferative disorder or disease caused, at least in part, by a virus.

Hence, the compounds described herein are optionally a nucleoside analog characterized as having an antiviral activity, conjugated to at least one acyl moiety derived from a carboxylic acid capable of inhibiting histone deacetylase.

Many nucleoside analogs used in anticancer chemotherapy target human enzymes, killing actively dividing cells, including both cancerous cells and other cells, thereby causing severe side effects. However, a nucleoside analog selective towards a viral enzyme would be expected to have fewer side effects, as only infected cells would be targeted. A nucleoside analog having an antiviral activity is therefore advantageous for an anti-proliferative treatment.

Exemplary carboxylic acids capable of inhibiting histone deacetylase include, without limitation, butyric acid (in which Ra and/or Rb is propyl), 4-phenylbutyric acid (in which Ra and/or Rb is 3-phenylpropyl), valproic acid (in which Ra and/or Rb is 4-heptyl), phenylacetic acid (in which Ra and/or Rb is phenylmethyl), 2-(4-isobutylphenyl)propionic acid, i.e. ibuprofen (in which Ra and/or Rb is 1-(4-isobutylphenyl)ethyl) and cinnamic acid (in which Ra and/or Rb is styryl).

Acyl moieties derived from these exemplary carboxylic acids are butyryl, 4-phenylbutyryl, valproyl, phenylacetyl, 2-(4-isobutylphenyl)propionyl and cinnamoyl, respectively.

The term "alkyl", as used herein, describes a saturated aliphatic hydrocarbon including straight chain and branched chain groups. In some embodiments, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. In some embodiments, the alkyl is a medium size alkyl having 1 to 10 carbon atoms. In some embodiments, the alkyl is a lower alkyl having 1 to 4 carbon atoms. The alkyl group may be substituted or unsubstituted. Substituted alkyl may have one or more substituents, whereby each substituent can independently be, for example, cycloalkyl, heteroalicyclic, aryl or heteroaryl.

The term "alkenyl", as used herein, describes an unsaturated aliphatic hydrocarbon having one or more unsaturated bonds, including straight chain and branched chain groups. In some embodiments, the alkenyl group has 2 to 20 carbon atoms. In some embodiments, the alkyl is a medium size alkenyl having 2 to 10 carbon atoms. In some embodiments, the alkenyl is a lower alkenyl having 2 to 4 carbon atoms. The alkenyl group may be substituted or unsubstituted. Substituted alkenyl may have one or more substituents, whereby each substituent can independently be, for example, cycloalkyl, heteroalicyclic, aryl or heteroaryl.

The term "cycloalkyl", as used herein, describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, alkyl, alkenyl, cycloalkyl, heteroalicyclic, aryl or heteroaryl.

The term "aryl", as used herein, describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent can independently be, for example, alkyl, alkenyl, cycloalkyl, heteroalicyclic, aryl or heteroaryl.

The term "heteroaryl", as used herein, describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent can independently be, for example, alkyl, alkenyl, cycloalkyl, heteroalicyclic, aryl or heteroaryl. Representative examples are pyridine, pyrrole, oxazole, indole, purine and the like.

The term "heteroalicyclic", as used herein, describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofuran, tetrahydropyran, morpholine and the like. The heteroalicyclic may be substituted or unsubstituted. Substituted heteroalicyclic may have one or more substituents, whereby each substituent can independently be, for example, alkyl, alkenyl, cycloalkyl, heteroalicyclic, aryl or heteroaryl.

Further optional substituents of alkyl, alkenyl, cycloalkyl, aryl, heteroaryl and heteroalicyclic groups include, for example, hydroxyalkyl, haloalkyl, alkynyl, amine, halide, sulfate, sulfonate, sulfonyl, sulfoxide, phosphoryl, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The term "alkynyl" describes a —C≡C—R' group, where R' is as defined hereinabove.

The terms "halide" and "halo" describe fluorine, chlorine, bromine or iodine.

The term "haloalkyl" describes an alkyl group as defined herein, which is substituted by one or more halides.

The term "hydroxyalkyl" describes an alkyl group as defined herein, further substituted by one or more hydroxyl group.

The term "sulfate" describes a —O—S(=O)$_2$—OR' group, where R' is as defined herein.

The term "sulfonate" describes a —S(=O)$_2$—OR' group, where R' is as defined herein.

The term "sulfonyl" describes a —S(=O)$_2$—R' group, where R' is as defined herein.

The term "sulfoxide" describes a —S(=O)—R' group, where R' is as defined herein.

The term "sulfonamide" describes a —S(=O)$_2$—NR'R" group and a R'S(=O)$_2$—NR"— group, with R' and R" as defined herein.

The term "phosphonate" describes a —P(=O)(OR')(OR") group, with R' and R" as defined herein.

The term "phosphoryl" describes a —O—P(=O)(OR')(OR") group, with R' and R" as defined herein.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "cyano" describes a —C≡N group.

The term "nitro" describes an —NO$_2$ group.

The term "N-carbamate" describes an —N(R)C(=O)—OR" group, with R' and R" as defined herein.

The term "O-carbamate" describes an —OC(=O)—NR'R" group, with R' and R" as defined herein.

The term "N-thiocarbamate" describes a —N(R)C(=S)—OR" group, with R' and R" as defined herein.

The term "O-thiocarbamate" describes a —OC(=S)—NR'R" group, with R' and R" as defined herein.

The term "urea", describes a —NR'C(=O)—NR"R''' group, where R' and R" are as defined herein and R''' is as defined herein for R' and R".

The term "thiourea", describes a —NR'—C(=S)—NR"R''' group, with R', R" and R" as defined herein.

The term "guanyl" describes a R'R"NC(=N)— group, where R' and R" are as defined herein.

The term "guanidine" describes a —R'NC(=N)—NR"R''' group, where R', R" and R''' are as defined herein.

The term "hydrazine" describes a —NR'—NR"R''' group, with R', R", and R''' as defined herein.

The term "azo" describes a —N=NR' group, with R' as defined herein.

As discussed hereinabove, in some embodiments of the present invention, the nucleoside analog is acyclovir or ganciclovir.

Thus, according to some embodiments of the present invention, there is provided a compound having Formula I:

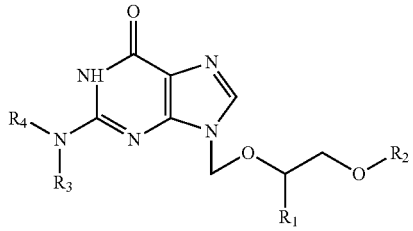

Formula I wherein:

R$_1$ is selected from the group consisting of H and —CH$_2$OR$_5$; and

R$_2$, R$_3$, R$_4$ and R$_5$ are each independently hydrogen or an acyl moiety selected from the group consisting of butyryl, valproyl, 4-phenylbutyryl, cinnamoyl, phenylacetyl, 2-(4-isobutylphenyl)propionyl, 1-(butyryloxymethoxy)succinyl, 1-(valproyloxymethoxy)succinyl, 1-(4-phenylbutyryloxymethoxy)succinyl, 1-(cinnamoyloxymethoxy)succinyl 1-(phenylacetoxymethoxy)succinyl and 1-(2-(4-isobutylphenyl)propionyloxymethoxy)succinyl provided that at least one of R$_2$, R$_3$ and R$_4$ is the acyl moiety selected from the group consisting of butyryl, valproyl, 4-phenylbutyryl, cinnamoyl, phenylacetyl, 2-(4-isobutylphenyl)propionyl, 1-(butyryloxymethoxy)succinyl, 1-(valproyloxymethoxy)succinyl, 1-(4-phenylbutyryloxymethoxy)succinyl, 1-(cinnamoyloxymethoxy)succinyl, 1-(phenylacetoxymethoxy)succinyl and 1-(2-(4-isobutylphenyl)propionyloxymethoxy)succinyl.

As discussed herein, compounds comprising acyl moieties derived from carboxylic acids capable of inhibiting HDAC have been found to have particularly potent anticancer effects. Butyric acid, valproic acid, 4-phenylbutyric acid, cinnamic acid, phenylacetic acid and 2-(4-isobutylphenyl)propionic acid are known to exhibit HDAC inhibition activity.

In one embodiment, R$_2$, R$_3$, R$_4$ and R$_5$ are each independently selected from the group consisting of hydrogen (H), butyryl, 4-phenylbutyryl, cinnamoyl and valproyl.

According to one embodiment of the present invention, R$_1$ is H, the compound being an acylated derivative of acyclovir.

In another embodiment, R$_1$ is —CH$_2$OR$_5$, the compound being an acylated derivative of ganciclovir.

In another embodiment of the present invention, R$_4$ is H.

Exemplary compounds include, without limitation, compounds in which R$_2$ and R$_3$ are each butyryl; compounds in which R$_2$ and R$_3$ are each cinnamoyl; compounds in which R$_2$ is valproyl and R$_3$ is H; compounds in which R$_2$ is 4-phenylbutyryl and R$_3$ is H; compounds in which R$_3$ is valproyl and R$_2$ is H; compounds in which R$_2$ is 2-(4-isobutylphenyl)propionyl and R$_3$ is H; compounds in which R$_2$ is phenylacetyl and R$_3$ is H; and compounds in which R$_2$ and R$_3$ are each valproyl.

According to an embodiment of the present invention, the compound is N-valproyl-9-(2-valproyloxy)ethoxymethylguanine (also referred to herein as Compound 6; see, Table 1 in the Examples section that follows).

As described hereinabove, whereas some acylated derivatives of nucleoside analogs have been taught in the context of antiviral therapy, the inventors of the present invention have surprisingly found that acylated derivatives of nucleoside analogs have strong anticancer properties.

According to another aspect of the embodiments of the present invention, there is provided a method of treating a proliferative disorder or disease, the method comprising administering to a subject in need thereof an effective amount of a compound having the formula:

A-X—B        Formula III wherein:

X is a purinic or pyrimidinic nucleoside analog having at least one hydroxyl group and/or at least one amino group, as described herein;

A is one or two acyl moieties attached to an amino group of said X or absent, as described herein; and B is an acyl moiety attached to a hydroxyl group of said X or absent, as described herein;

each of said acyl moieties, if present, being independently selected from the group consisting of a —C(=Y$_1$)—Ra group and a —C(=Y$_2$)-L-C(=Y$_3$)—OCH$_2$C(=Y$_4$)—Rb group, as described herein.

According to another aspect of the embodiments of the present invention, there is provided a use of a compound described hereinabove in the manufacture of a medicament for the treatment of a proliferative disorder or disease.

In any of the different embodiments described herein, the derivatives of nucleoside analogs described herein can be utilized either per se, or as part of a pharmaceutical composition where it is mixed with a pharmaceutically acceptable carrier.

Thus, according to additional aspects of the present invention, there is provided a pharmaceutical composition, which comprises one or more compounds described hereinabove, and a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to the subject treated.

Hereinafter, the phrases "physiologically acceptable carrier" and "pharmaceutically acceptable carrier" which may be interchangeably used refer to a carrier or a diluent that does not cause significant irritation to the subject and does not abrogate the biological activity and properties of the administered compound. As used herein, the term "carrier" refers to a diluent, adjuvant, excipient, or vehicle with which the therapeutic is administered.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophthalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of a proliferative disorder or disease.

Thus, according to an embodiment of the present invention, the pharmaceutical composition of the present invention is being packaged in a packaging material and identified in print, in or on the packaging material, for use in the treatment of a proliferative disorder or disease.

As used herein, the phrase "proliferative disease or a disorder" describes an abnormal, undesired physiological condition in mammals that is typically characterized by unregulated and oftentimes aggressive cell growth and/or division, which occurs without respect to normal cell or tissue limits. Some proliferative diseases are also characterized by invasive cell growth and/or division, which invade and destroy adjacent tissues, and/or sometimes metastatic proliferation, which spreads to other locations in the body. Cell proliferation conditions which may be treated by the compounds of the present invention include, for example, malignant tumors such as cancer, and benign tumors.

Proliferative disorders or diseases (e.g., cancer) which are characterized as being caused, at least in part, by a virus are exemplary conditions suitable for treatment according to embodiments of the present invention.

An exemplary virus which causes cancer is Epstein-Barr virus, which is associated with cancers such as Burkitt's lymphoma, Hodgkin's lymphoma, B lymphoproliferative disease and nasopharyngeal carcinoma. Other viruses associated with cancer include, without limitation, hepatitis B and hepatitis C viruses (associated with, e.g., liver cancer), human T-lymphotrophic virus (associated, e.g., with tropical spastic paraparesis and adult T-cell leukemia), human papillomaviruses (associated, e.g., with cervical cancer, skin cancer, anal cancer and penis cancer) and Kaposi's sarcoma-associated virus (associated with, e.g., Kaposi's sarcoma and body cavity lymphoma).

Non-cancerous proliferative conditions caused by viruses include, for example, warts.

As used herein, the term "cancer" refers to various types of malignant neoplasms, most of which can invade surrounding tissues, and may metastasize to different sites, as defined by Stedman's medical Dictionary 25th edition (Hensyl ed., 1990).

Various cancer types are treatable according to embodiments of the present invention, including, for example, a sarcoma, a leukemia, a carcinoma and/or an adenocarcinoma. Exemplary cancers include, without limitation, breast cancer, hepatoma, liver cancer, pancreatic carcinoma, oesophageal carcinoma, bladder cancer, gastrointestinal cancer, T-cell leukemia, Kaposi's sarcoma, squamous cell carcinoma (SCC) of the skin, pulmonary carcinoma, ovarian cancer, skin cancer, prostate cancer, Ewing's sarcoma and gastric cancer.

In addition to benign tumors, other non-cancerous proliferative disorders are also treatable using the compounds of the present invention. Such non-cancerous proliferative disorders include, for example, stenosis, restenosis, in-stent stenosis, vascular graft restenosis, arthritis, rheumatoid arthritis, diabetic retinopathy, angiogenesis, pulmonary fibrosis, hepatic cirrhosis, atherosclerosis, glomerulonephritis, diabetic nephropathy, thrombic microangiopathy syndromes and transplant rejection.

According to further embodiments of the any of the methods, uses and compositions presented herein, the compounds of the present invention can be combined with other active ingredients which are commonly used to treat proliferative diseases and disorders.

Exemplary active ingredients used to treat proliferative diseases and disorders include, without limitation, chlorambucil, chlormethine, cyclophosphamide, ifosfamide, melphalan, bendamustine, carmustine, fotemustine, lomustine, streptozocin, carboplatin, cisplatin, oxaliplatin, BBR3464, satraplatin, busulfan, dacarbazine, procarbazine, temozolomide, thioTEPA, treosulfan, uramustine, aminopterin, methotrexate, pemetrexed, raltitrexed, cladribine, clofarabine, fludarabine, mercaptopurine, pentostatin, thioguanine, capecitabine, cytarabine, fluorouracil, floxuridine, gemcitabine, docetaxel, paclitaxel, vinblastine, vincristine, vindesine, vinorelbine, daunorubicin, adriamycin (doxorubicin), epirubicin, idarubicin, mitoxantrone, pixantrone, valrubicin, actinomycin, bleomycin, mitomycin, plicamycin, hydroxyurea, camptothecin, topotecan, irinotecan, rubitecan, etoposide, teniposide, cetuximab, panitumumab, trastuzumab, rituximab, tositumomab, alemtuzumab, bevacizumab, gemtuzumab, aminolevulinic acid, methyl aminolevulinate, porfimer sodium, verteporfin, cediranib, dasatinib, erlotinib, gefitinib, imatinib, lapatinib, nilotinib, sorafenib, sunitinib, vandetanib, alitretinoin, tretinoin, altretamine, amsacrine, anagrelide, arsenic trioxide, asparaginase, pegaspargase, bexarotene, bortezomib, denileukin diftitox, estramustine, ixabepilone, masoprocol, mitotane and testolactone.

It is expected that during the life of a patent maturing from this application many relevant nucleoside analogs and histone deacetylase inhibitors will be developed and the scope of the phrases "nucleoside analog" and "carboxylic acid capable of inhibiting histone deacetylase" is intended to include all such new technologies a priori.

The terms "comprises", "comprising", "includes", "including", "having" and their conjugates mean "including but not limited to".

The term "consisting of" means "including and limited to".

As used herein, the singular form "a", an and the include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non-limiting fashion.

Materials and Methods

Materials:
Acyclovir is obtained from commercial vendors such as Sigma-Aldrich;
annexin V-FITC was obtained from MBL (Japan) as part of a MEBCYTO apoptosis kit;
ATP was obtained from Sigma-Aldrich;
bovine serum albumin (BSA) was obtained from Sigma-Aldrich;
butyryl chloride was obtained from Sigma-Aldrich;
bromophenol blue was obtained from Sigma-Aldrich;
dichlorodihydrofluorescein diacetate (DCF-DA) was obtained from Sigma-Aldrich;
4-dimethylaminopyridine (DMAP) was obtained from Sigma-Aldrich;
dithiothreitol (DTT) was obtained from Sigma-Aldrich;
glucose was obtained from Sigma-Aldrich;
glycerol was obtained from Sigma-Aldrich;
horseradish peroxidase-goat anti-rabbit IgG antibody was obtained from Jackson ImmunoResearch Labs Inc. (West Grove, Pa., USA);
horseradish peroxidase-rabbit anti-mouse IgG antibody was obtained from Jackson ImmunoResearch Labs Inc. (West Grove, Pa., USA);

JC-1 was obtained from Calbiochem-Novabiochem (La Jolla, Calif., USA);

Lactate dehydrogenase was obtained from Sigma-Aldrich;

leupeptin was obtained from Sigma-Aldrich;

mouse monoclonal anti-actin antibody was obtained from MP Biomedicals (Ohio, USA);

mouse monoclonal anti-human p21 antibody was obtained from Cell Signaling Technology Inc. (USA);

mouse monoclonal anti-phospho-H2AX (Ser139) antibody was obtained from BioLegend (San Diego, USA);

MTT was obtained from Sigma-Aldrich;

NADH was obtained from Sigma-Aldrich;

Nonidet® NP-40 was obtained from Sigma-Aldrich;

N-succinyl-Leu-Leu-Val-Tyr-7-amido-4-methylcoumarin was obtained from Sigma-Aldrich;

pepstatin was obtained from Sigma-Aldrich;

phosphoenolpyruvate was obtained from Sigma-Aldrich;

PMSF was obtained from Sigma-Aldrich;

propidium iodide was obtained from MBL (Japan) as part of a MEBCYTO apoptosis kit;

pyridine was obtained from Sigma-Aldrich;

pyruvate kinase was obtained from Sigma-Aldrich;

rabbit anti-acetyl-histone H4 (Lys12) and rabbit polyclonal anti-human anti-histone H3 antibodies were obtained from Cell Signaling Technology Inc. (USA);

sodium deoxycholate was obtained from Sigma-Aldrich;

sodium dodecyl sulfate (SDS) was obtained from Sigma-Aldrich;

sodium orthovanadate was obtained from Sigma-Aldrich;

Tris-HCl was obtained from Sigma-Aldrich;

valproic acid is obtained from commercial vendors such as Acros Organics;

valproyl chloride was prepared by treating valproic acid with oxalyl chloride, obtained from Sigma-Aldrich.

All other solvents and reagents used were obtained from known vendors such as Sigma-Aldrich.

All commercial chemicals and solvents were reagent grade and were used without further purification unless otherwise specified.

Analytical Measurements:

Melting points are uncorrected.

$^1$H and $^{13}$C NMR spectra 200-MHz and 300-MHz were obtained on Bruker AC-200 and AM-300 spectrometers, respectively, according to the manufacturer's instructions. Chemical shifts are expressed in ppm downfield from Me$_4$Si used as internal standard. The values are given in δ scale.

High-resolution mass spectrometry (HRMS) measurements were obtained on a VG AutoSpec E spectrometer.

Progress of the reactions was monitored by TLC on silica gel (Merck, Art. 5554) or alumina (Riedel-de Haen, Art. 37349). Silica gel 60 F254 plates were used for analytical TLC (visualized with UV light and iodine vapors); flash column chromatography was performed on silica gel 60 ((Merck, Art. 9385; 70-230 mesh).

Elemental analyses were obtained on a FlashEA 1112 Elemental ANlyzer (Thermo Scientific).

Cells:

The human cell lines used in this study were: prostate carcinoma 22RV1, glioblastoma U251 and U87 MG, primary human and rat astrocytes, human myelocytic leukemia HL-60 (CCL-240) and the human breast carcinoma MCF-7 and MCF-7 DX. The murine D122 clone of 3LL Lewis lung carcinoma cells was selected for highly metastatic properties, as was murine breast carcinoma 4T1 (ATCC). The cell lines were grown in Roswell Park Memorial Institute medium (RPMI-1640), except for MCF-7 cells which were grown in Dulbecco's modified Eagle's medium (DMEM) supplemented with penicillin (250 µg/mL) and streptomycin (125 µg/mL), L-glutamine (2 mM) and 10% fetal calf serum (FCS). The cells were transferred twice weekly and grown at 37° C. in a humidified 5% $CO_2$ incubator. All cell culture reagents were purchased from Biological Industries (Beit Haemek, Israel).

Viability Assay:

Cells (in quadruplicate) at the specified density were suspended in 200 µL medium supplemented with 10% FCS seeded in 96-well plates for 24 hours, then exposed to the drugs for 72 hours. The viability of the cells was determined by Hoechst fluorescent assay as described by Nudelman et al., 2005. Leukemic cell viability after 72 hours of treatment was determined by an MTT (3-(4,5-dimethylthiazol-2-yl)-2,5-diphenyltetrazolium bromide) assay as described by Levovich et al., 2007.

Isolation of Primary Rat Astrocytes:

Brains were removed from neonatal rats, and the cerebral cortex was dissected and minced. The cells were dissociated by vigorous shaking in DMEM supplemented with 20% FCS, and cells from 3 brains were seeded in 20 mL of the medium. After one week, the serum concentration was reduced to 10%. The cells in the culture exhibited typical neuronal and astrocyte morphology.

Isolation of Primary Rat Cardiomyocytes:

Neonatal rat ventricular cardiomyocytes were isolated and cultured in collagen coated culture dishes as described by Shalitin et al., 1996. Growth medium contained DMEM:Ham's F12 (1:1), fetal calf serum (10%) and antibiotics. Treatment was administered to spontaneously beating cardiomyocytes 48 hours after plating.

Assessment of Changes in Mitochondrial Membrane Potential ($\Delta\psi_m$):

The fluorescent mitochondrial-specific cationic dye JC-1 undergoes potential-dependent accumulation in the mitochondria. HL-60 cells ($1\times10^6$) were treated for 24 hours with the corresponding prodrugs, centrifuged and resuspended in 0.5 mL of 40 mM HEPES buffer, pH 7.4, supplemented with 0.65% NaCl and 4.5 g/L glucose (Buffer A) at 37° C., containing 1 µg/mL JC-1. The cells were incubated for 15 min at 37° C., washed and resuspended in 200 µL of dye free Buffer A, added to a 96-well black plate (Greiner Bio-one, Germany) and the fluorescence was measured immediately (FluoStar fluorometer, BMG Labtech, Germany) using excitation/emission filters of 485/540 nm (green); 540/590 nm (red). The ratio of red/green fluorescence was calculated.

Detection of Reactive Oxygen Species (ROS) and Nitrogen Reactive Species (RNS):

U251 cells ($5\times10^4$) were seeded in 24 well plates, and after 24 hours washed and resuspended in PBS. The tested compounds were added for 1.5 hours and the determination of nitrate and nitrite levels was performed using a fluorometric Nitric Oxide Assay Kit® (Calbiochem) according to the manufacturers protocol. Fluorescence was measured with excitation/emission filters of 390/440 nm in a FluoStar fluorimeter. The concentration of nitrate was determined by subtracting the nitrite concentration from the total concentration of nitrite+nitrate.

ROS levels were determined by FACS analysis of U-251 cells treated with dichlorodihydrofluorescein diacetate (DCF-DA), which becomes fluorescent when oxidized.

Histone Acetylation:

For the determination of in vitro histone acetylation, 2.5-$3\times10^6$ cells, seeded in 100 mm culture dishes, were supplemented with RPMI medium containing 10% heat inactivated FCS and were treated with the drugs the following day. At the specified times post-treatment, the cells were removed with a rubber policeman, centrifuged, washed, lysed with lysis buffer (PBS, Nonidet® NP-40 1%, sodium deoxycholate 0.5%, sodium dodecyl sulfate (SDS) 0.1%, 1 mM phenylmethylsulfonyl fluoride (PMSF), 1 mM sodium orthovanadate, and 1 µM each of leupeptin and pepstatin) and centrifuged at 10,000 g for 10 minutes at 4° C. The supernatant was subjected to acid extraction with $H_2SO_4$ (0.2 M) for 1 hour, dialyzed against 0.1 M acetic acid for 2 hours and then against double distilled water three times (2 hours each). The extract was then lyophilized, and protein concentration was determined with a BCA kit (Pierce, USA). For the evaluation of in vivo histone acetylation, mice were treated as specified and sacrificed, and their tumors were removed and frozen immediately in liquid nitrogen and kept at –70° C. When the tumor tissue thawed, the extract was homogenized. The fold increase of acetylated histones was determined by the ratio of band intensities of treated and untreated cells or mice, normalized to loading control (total histone H3).

Western Blot Analysis:

Cell lysates or acid extracted histones were solubilized in a concentrated (×4) loading buffer (62.5 mM Tris-HCl, pH 6.8, 1% SDS, 10% glycerol v/v, 1% dithiothreitol (DTT) and 0.1 mg/ml bromophenol blue). Proteins (10-40 µg) were run on SDS-PAGE, transferred to a nitrocellulose membrane (Schleicher & Schuell, Germany) and probed with the primary antibodies, followed by incubation with a horseradish peroxidase (HRP)-goat anti-rabbit IgG or HRP-rabbit anti-mouse IgG as secondary antibodies. HRP bound to the secondary antibodies was visualized by the enhanced chemiluminescence method using the Western Blotting Luminol reagent (Santa Cruz, Calif., USA). The membrane was exposed for 5 minutes to Chemiluminescence BioMax light film (Kodak, USA) and the intensity of the bands was measured with a VersaDoc instrument with a Quantityl program (Bio-Rad, USA). The fold increase of each specific protein was determined by the ratio of band intensities of treated and untreated cells, normalized to loading control (actin or total histone H3).

Apoptosis Measurement by Annexin V-FITC and Propidium Iodide Staining:

Cells were seeded in six-well plates ($10^5$ cells/well) for 24 hours and were then treated as specified, trypsinized, washed with PBS, double-stained with annexin V-FITC (fluorescein isothiocyanate) and propidium iodide, according to the manufacturer's instructions and subjected to flow cytometry analysis (FACScalibur cytometer, Becton Dickinson).

Cell Cycle Analysis:

Cells ($4 \times 10^5$) were seeded in 35 mm culture dishes and after 24 hours were starved in medium without serum for an additional 24 hours, and then treated with the drug for an additional 24 hours. The cells were then trypsinized to a single cell suspension in PBS, washed, and resuspended in PBS at a concentration of $10^6$ cells/mL. The cells were fixed with 70% ethanol for 30 minutes at 4° C., centrifuged and resuspended in 1 ml PBS containing 0.1% Tween 20 and 0.05% bovine serum albumin (BSA). RNase free of DNase was added, and the cell suspension ($10^6$ cells) was incubated at 3° C. for 30 minutes. The cell suspension was then chilled on ice to a temperature in the range of 2 to 8° C. Propidium iodide (50 µg/mL) was added to the cell suspension, which was than kept in the dark. Red fluorescence (>630 nm) was analyzed on the flow cytometer.

Proteasome Activity Assay:

The peptidase or chymotrypsin-like activity of the proteasome was assayed using N-succinyl-Leu-Leu-Val-Tyr-7-amido-4-methylcoumarin. The lysates (100 µL) were incubated with 13 (M of the substrate in 100 mM Tris, pH 7.5, for 1 hour with shaking at room temperature. The reaction was stopped by addition of ice-cold ethanol, and the samples were centrifuged for 5 minutes at 2500 g. The supernatants were collected and the fluorescence was measured with excitation/emission filters of 390/460 nm using the FluoStar fluorimeter. The protein concentration was determined using a BCATM kit (Pierce) and the proteasome activity was derived from the ratio of fluorescence at 460 nm/(g of protein. The percentage of proteasome activity was calculated relative to untreated cells.

Viral Thymidine Kinase Activity:

Viral thymidine kinase (V-TK) has a broad specificity and acts on thymidine as well as a wide spectrum of nucleoside analogs, including acyclovir and ganciclovir. The mammalian thymidine kinase (TK) has a narrow specificity and acts only on thymidine. To detect V-TK activity, cancer cells were treated with acyclovir or its analogs for 24 hours, harvested, washed and suspended in cold Tris buffer 10 mM, pH 7.5, followed by 5 cycles of freeze-thaw, and centrifuged (4° C., 16,000 RPM). The lysates obtained were kept at –70 ° C. until analyzed either spectroscopically or by RT-PCR.

Figure 1:
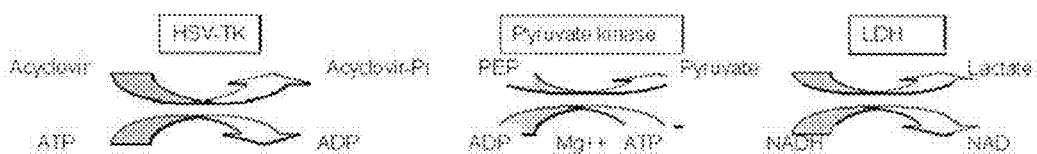

As shown schematically in FIG. 1, V-TK phosphorylates acyclovir and converts ATP to ADP. The ADP is converted to ATP by pyruvate kinase when it hydrolyzes phosphoenolpyruvate (PEP) to pyruvate. Lactate dehydrogenase then converts pyruvate to lactate and NADH to $NAD^+$.

The decrease in fluorescence emitted by NADH (excitation/emission of 320/460 nm) during 10 cycles, each lasting 1 minute, were monitored using a FluoStar fluorometer. The reaction velocity was determined by the slope of the fluorescence vs. time.

PCR Assay for the Detection of HSV-TK Gene Expression:

Expression of HSV-TK gene in cells was analyzed by PCR as described by Bailout et al., 2007.

Metastatic Lewis Lung Carcinoma Model:

Female C57/BL mice, 7-10 weeks old, were acclimated for ten days. All in vivo experiments were conducted according to the NIH Laboratory Animal Care Guidelines and in accordance with the guidelines and approval of the Tel Aviv University Committee for Animal Experimentation.

Metastatic Breast Carcinoma Model:

The syngeneic murine breast carcinoma metastatic model was performed with 8-10 weeks old BALB-c mice implanted with 4T1 cells. When the tumor volume reached 75-180 $mm^3$ (after ~10 days), treatment was initiated for an additional 21 days. At termination, the animals were sacrificed and their lungs removed, stained with Bouin's solution, and lung lesions were scored under an illuminated magnifying glass.

Acute Toxicity Assay in Mice:

Male ICR mice, 8 weeks old (Harlan, Israel) were acclimated for 10 days before administration of the tested compounds. The animals were monitored for two weeks and weighed three times per week.

Data Analysis:

$IC_{50}$ values were determined by linear regression of the percentage of survival following drug titration.

The significance of the effects in comparative studies was determined by a Student's t-test.

The combination index for drug interaction was calculated by Chou's Median Effect Analysis (MEA) [Chou, 2006]. The combination index (CI) was defined as CI=D1/(DM)1+D2/(DM)2, where D1 and D2 are the doses of drug 1 and drug 2, respectively, (DM)1 and (DM)2 are the doses of drug 1 and drug 2 and their mixture (in a specified ratio) required to produce a median effect, e.g., IC50. CI<1, =1 or >1 indicates synergism, additive effect, and antagonism respectively.

Chemical Syntheses

Synthesis of O-monoacylated Nucleoside Analogs—General Procedure:

Approximately 2 equivalents of 4-dimethylaminopyridine (DMAP), e.g. in tetrahydrofuran, is added under argon to a suspension of a nucleoside analog (e.g. acyclovir) comprising a hydroxyl group (1 equivalent). The mixture is stirred for a few minutes and approximately 2 equivalents of an acyl chloride is added slowly over the course of a few minutes. The mixture is then stirred overnight, the solvent is removed, and the resulting residue is re-crystallized in a polar solvent (e.g. ethanol) to give the product.

Using this general procedure, the compounds AN-449, AN-451, AN-452 and AN-454 (see Table 1) have been prepared.

In a typical example, 9-(2-valproyloxy)ethoxymethylguanine (AN-452) was prepared as follows:

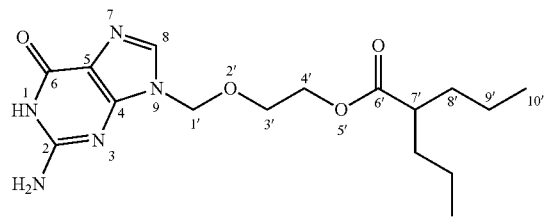

9-(2-Valproyloxy)ethoxymethylguanine (AN-452)

250 mg (2.05 mmol) of DMAP (4-dimethylaminopyridine) in 10 mL tetrahydrofuran (THF) was added to a suspension of acyclovir (225 mg, 1 mmol) under argon. The resulting suspension was stirred for a few minutes and valproyl chloride (0.35 mL, 2.05 mmol) was added dropwise over the course of 5 minutes. The suspension then became thicker and was stirred overnight. The solvent was removed and the resulting yellowish solid residue was re-crystallized in ethanol to give AN-452 (230 mg, 65% yield) as white crystals. m.p.=219-222° C.

$^1$H-NMR (DMSO-d$_6$): δ =10.66 (s, 1H, H-1), 7.80 (s, 1H, H-8), 6.53 (s, 2H, H-10), 5.34 (s, 2H, H-1'), 4.11 (m, 2H, H-4'), 3.65 (m, 2H, H-3'), 2.26 (m, 1H, H-7'), 1.36 (m, 4H, H-8'), 1.16 (sex, J=7.2 Hz, 4H, H-9'), 0.81 (t, J=7.2 Hz, 6H, H-10') ppm.

$^{13}$C-NMR (DMSO-d$_6$): δ =175.4 (C-6'), 156.8 (C-6), 153.9 (C-2), 151.4 (C-4), 137.6 (C-8), 71.7 (C-1'), 66.7 (C-4'), 62.4 (C-3'), 44.3 (C-7'), 35.0 (C-8'), 19.9 (C-9'), 13.8 (C-10') ppm.

Elemental analysis: calculated for C$_{16}$H$_{25}$N$_5$O$_4$ (351.4) C, 54.69; H, 7.17; N, 19.93. found C, 51.70; H, 7.26; N, 19.58.

Synthesis of N-monoacylated Nucleoside Analogs—General Procedure:

A nucleoside analog comprising an amine group (e.g. acyclovir) is suspended in pyridine and trimethylsilyl chloride is added in excess. The mixture is stirred for a few minutes, and an acyl chloride is then added gradually at a concentration approximately equimolar to the nucleoside analog amine group. The solution is stirred overnight at room temperature and then cooled to 0-(−5)° C. and distilled water is added. The solution is stirred overnight at room temperature. The solvent is then removed and the residue suspended in distilled water. The aqueous suspension is extracted with ethyl acetate:ether solution. The organic layer that contains the product is separated and evaporated. The solid is then washed with a non-polar solvent (e.g. n-hexane) and dried under vacuum. The solid is then re-crystallized in a polar solvent (e.g. methanol) to give the product.

In a typical example, AN-463 has been prepared as follows:

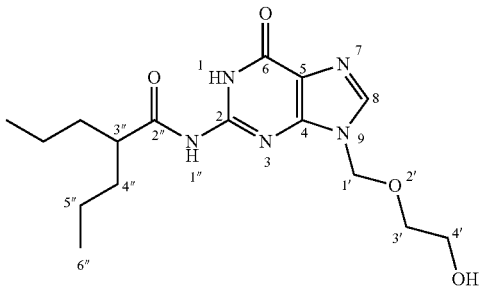

N-Valproyl-9-(2-hydroxy)ethoxymethylguanine (AN-463)

Acyclovir (0.5 gram, 2.22 mmol) was suspended in pyridine (50 mL) and trimethylsilyl chloride (1.2 mL, 9.4 mmol) was added. The mixture was stirred for 15 minutes, after which a clear solution formed, and valproyl chloride (0.5 mL, 2.95 mmol) was then added over the course of 3 minutes. The yellowish clear solution was stirred overnight at room temperature. The solution was then cooled to 0-(−5)° C. and distilled water (10 mL) was added. The slightly yellowish, clear solution was stirred overnight at room temperature. The solvent was then removed and the residue was suspended in distilled water (50 mL). The aqueous suspension was extracted with ethyl acetate:ether solution (3×30 mL). The organic layer that contained a pink precipitate was separated and evaporated to give a pink powder. The solid was washed thrice with n-hexane (10 mL) and dried under vacuum. The solid was then re-crystallized in methanol to give AN-463 (560 mg, 72% yield) as pink crystals.

$^1$H-NMR (MeOD): δ =8.16 (s, 1H, H-8), 5.62 (s, 2H, H-1'), 3.67 (m, 4H, H-4'+H-3'), 2.26 (m, 1H, H-3"), 1.72+1.52 (m, 4H, H-4"), 1.38 (m, 4H, H-5"), 0.97 (t, J=Hz, 6H, H-6") ppm.

$^{13}$C-NMR (MeOD): δ =182.1 (C-2"), 158.3 (C-6), 151.8 (C-2), 150.6 (C-4), 142.5 (C-8), 121.7 (C-5) 75.2 (C-1'), 73.1 (C-4'), 62.74 (C-3'), 49.2 (C-3"), 36.8 (C-4"), 22.5 (C-5"), 15.2 (C-6") ppm.

Synthesis of N,O-Bis-Acylated Nucleoside Analogs—General Procedure:

A molar excess of both DMAP and a base (e.g. triethylamine) are added to a suspension of a nucleoside analog comprising a hydroxyl group and an amine group (e.g. acyclovir) in a non-polar solvent (e.g. CH$_2$Cl$_2$) under argon at approximately 0° C. The resulting mixture is stirred for a few minutes and a molar excess of acyl chloride in the non-polar solvent is added gradually. The solution is brought to room temperature and then stirred for approximately 2 hours. The mixture is quenched with water and diluted with the non-polar solvent. The resulting mixture is washed with acid (e.g. 5% HCl solution), followed by a base (e.g. saturated NaHCO$_3$ solution) and a neutral solution (e.g. brine). The organic layer is dried and evaporated. The resulting solid is re-crystallized from a solvent such as ethanol or diethyl ether to give the N,O-bis-acylated product.

The procedure described above results in a bis-acylated product with identical acyl groups. A monoacylated nucleoside analog may be used instead of a non-acylated nucleoside analog as a starting material in the above procedure in order to obtain a bis-acylated product with non-identical acyl groups.

Using this general procedure, the compounds AN-446, AN-447, AN-448, AN-460 and AN-462 (see Table I) have been prepared.

In a typical example, N-valproyl-9-(2-valproyloxy) ethoxymethylguanine (AN-446) was prepared as follows:

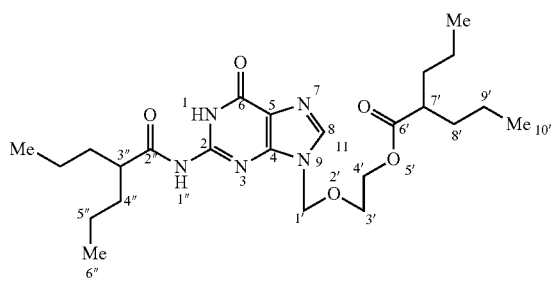

N-Valproyl-9-(2-valproyloxy)ethoxymethylguanine (AN-446)

To a suspension of acyclovir (6.67 mmol) in 60 mL $CH_2Cl_2$ at 0° C. and under argon, DMAP (5 equivalents) and triethylamine (5 equivalents) were added. The resulting mixture was stirred for a few minutes and valproyl chloride (5 equivalents) in 20 mL $CH_2Cl_2$ was added dropwise over the course of 5 minutes. The yellowish solution was brought to room temperature and then stirred for 2 hours. The mixture was quenched with water and diluted with $CH_2Cl_2$. The resulting mixture was washed thrice with 5% HCl solution (50 mL), twice with saturated $NaHCO_3$ solution (50 mL) and once with brine (50 mL). The organic layer was dried over $MgSO_4$ and evaporated.

The resulting off-white solid was re-crystallized from ethanol, to give AN-446 as white crystals (850 mg, 27% yield). m.p.=113-115° C.

$^1$H-NMR ($CDCl_3$): δ =9.38 (s, 1H, H-1), 8.14 (s, 1H, H-8), 5.54 (s, 2H, H-1'), 4.26 (t, J=5.1 Hz, 2H, H-4'), 3.78 (t, J=5.1 Hz, 2H, H-3'), 2.54 (m, 1H, H-3"), 2.35 (m, 1H, H-7'), 1.97 (m, 2H, H-3), 1.69+1.53 (m, 4H, H-4"+4H, H-8'), 1.39+1.29 (m, 4H, H-5"+4H, H-9'), 0.92 (t, J=6.98 Hz, 3H, H-6"), 0.83 (t, J=7.9 Hz, 3H, H-10') ppm.

$^{13}$C-NMR ($CDCl_3$): δ =178.3 (C-2"), 176.5 (C-6'), 154.9 (C-6), 148.3 (C-2), 139.1 (C-8), 120.2 (C-5), 118.0 (C-4), 73.22 (C-1'), 67.72 (C-3'), 62.23 (C-4'), 48.28 (C-3"), 45.11 (C-7'), 34.64 (C-4"), 34.49 (C-8'), 20.60 (C-5"), 20.54 (C-9'), 13.95 (C-6"+C-10') ppm.

HRMS: calculated for $C_{24}H_{40}N_5O_5$ ($MH^+$, $DCl/CH_4$) 478.3029. found 478.3034.

Elemental analysis: calculated for $C_{24}H_{40}N_5O_5$ (477.295) C, 60.36; H, 8.23; N, 14.66; O, 16.75. found C, 60.45; H, 8.77; N, 15.07; O, 17.26.

Using butyryl chloride as the acyl chloride in the procedure described above, N-butyryl-9-(2-butyryloxy)ethoxymethylguanine (AN-447, see, Table 1) was obtained as white crystals recrystallized from ethanol (280 mg, 20% yield). m.p.=153-155° C.

$^1$H-NMR ($CDCl_3$): δ =12.32 (bs, 1H, H-1), 10.0 (s, 1H, H-1), 8.40 (s, 1H, H-8), 5.65 (s, 2H, H-1'), 4.26 (dd, J=4.5 Hz, 2H, H-4'), 3.83 (dd, J=4.5 Hz, 2H, H-3'), 2.54 (t, J=7.5 Hz, 1H, H-3"), 2.24 (t, J=7.5 Hz, 1H, H-7'), 1.72 (tq, J=7.5, 7.2 Hz 1H, H-4"), 1.60 (tq, J=7.5, 7.2 Hz, 2H, H-8), 1.01 (t, J=7.2 Hz, 2H, H-5"), 0.93 (t, J=7.2 Hz, 2H, H-9') ppm.

$^{13}$C-NMR ($CDCl_3$): δ =175.7 (C-2"), 173.7 (C-6'), 155.4 (C-6), 148.6 (C-2), 139.3 (C-8), 120.2 (C-5), 73.2 (C-1'), 67.8 (C-3'), 62.7 (C-4'), 39.1 (C-3"), 36.1 (C-7'), 34.64 C-4"+C-8'), 13.6 (C-5"+C-9') ppm.

HRMS: calculated for $C_{16}H_{23}N_5O_5$ ($M^+$, $DCl/CH_4$) 365.1699. found 365.1695.

Elemental analysis: calculated for $C_{16}H_{23}N_5O_5$ (365.169) C, 52.59; H, 6.34; N, 19.17. found C, 53.30; H, 6.39; N, 19.82.

Synthesis of Acylated Nucleoside Analogs with Methoxy-dicarboxylate Linker—General Procedure:

An acyloxymethyl halide (e.g. chloromethyl butyrate) is added to an approximately equimolar amount of a dicarboxylic acid (e.g. succinic acid) in a polar solvent (e.g. acetone) with approximately 2 equivalents of a base (e.g. triethylamine). The mixture is refluxed for a few hours (e.g. 12 hours), and a precipitate is formed. The precipitate is filtered and washed with the solvent. The filtrate is then dried by evaporation and the residue is partitioned between a slightly basic (e.g. pH 8) aqueous phase and an organic phase (e.g. ethyl acetate).

The aqueous phase is extracted several times with the organic phase while maintaining the basic pH of the aqueous phase by adding a base (e.g. potassium carbonate). The aqueous phase is then acidified (e.g. with 2 M HCl) and extracted with an organic solvent (e.g. ethyl acetate). The organic solvent is then treated with charcoal, dried and evaporated to give an acyloxymethyl-dicarboxylic acid monoester.

The acyloxymethyl-dicarboxylic acid monoester is esterified with a nucleoside analog or an N-acylated nucleoside analog in the presence of a base (e.g. triethylamine) and DMAP in an inert solvent (e.g. ethyl acetate or dichloromethane). The precipitate formed is washed and the product is then purified by chromatography or crystallization.

In an alternative method, a nucleoside analog or N-acylated nucleoside analog is esterified with a dicarboxylic acid by reacting with a corresponding anhydride (e.g. succinic anhydride). The resulting intermediate is then mixed with an acyloxymethyl halide in a polar solvent (e.g. dimethylformamide, acetone) in the presence of a base (e.g. triethylamine), to give the final product.

In another alternative procedure, succinic anhydride is reacted with benzyl alcohol to give benzyl succinate. Benzyl succinate is reacted with an acyloxymethyl halide to give a mono-acyloxymethyl ester-mono-benzyl ester of succinic acid. The mono-acyloxymethyl ester-mono-benzyl ester of succinic acid is hydrogenated using a palladium/charcoal catalyst, to give a mono-acyloxymethyl ester of succinic acid, which is then treated with oxalyl chloride to give the mono-acyloxymethyl ester of succinyl chloride. Reaction of the mono-acyloxymethyl ester of succinyl chloride with a nucleoside analog or an N-acylated nucleoside analog gives the corresponding acyloxymethyl-succinoyl ester of the nucleoside analog or the N-acylated nucleoside. The procedure can be performed using an anhydride of a dicarboxylic acid other than succinic acid as a starting material in order to generate acylated nucleoside analogs with other methoxy-dicarboxylate linkers.

Table 1 below presents the chemical structures and names of exemplary compounds according to some embodiments of the invention, prepared using the general procedures described herein.

TABLE 1

| Comp. No. | Comp. Name | M.W. | Comp. Structure |
|---|---|---|---|
| AN-446 Comp. 6 | N-valproyl-9-(2-valproyloxy) ethoxymethyl-guanine | 477.59 | |
| AN-447 Comp. 7 | N-butyryl-9-(2-butyryloxy) ethoxymethyl-guanine | 365.38 | |
| AN-448 Comp. 8 | N-octanoyl-9-(2-octanoyloxy) ethoxymethyl-guanine | 477.6 | |
| AN-449 Comp. 9 | 9-(2-(2-(4-isobutylphenyl)-propionyloxy))-ethoxymethyl-guanine | 413.47 | |
| AN-451 Comp. 11 | 9-(2-(4-phenyl-butyryloxy))-ethoxymethyl-guanine | 371.39 | |
| AN-452 Comp. 12 | 9-(2-valproyloxy) ethoxymethyl-guanine | 351.4 | |
| AN-454 Comp. 14 | 9-(2-(phenyl-acetoxy))-ethoxymethyl-guanine | 343.34 | |

TABLE 1-continued

| Comp. No. | Comp. Name | M.W. | Comp. Structure |
|---|---|---|---|
| AN-460 Comp. 20 | N-hexanoyl-9-(2-hexanoyloxy)-ethoxymethyl-guanine | 421.49 | |
| AN-462 Comp. 22 | N-cinnamoyl-9-(2-cinnamoyloxy)-ethoxymethyl-guanine | 485.49 | |
| AN-463 Comp. 23 | N-valproyl-9-(2-hydroxy)ethoxymethyl-guanine | 351.4 | |

Results

In Vitro Studies:
Viability Assays:

The in vitro anti-cancer activity of acyclovir and Compound 6, an N,O-bis-acylated acyclovir, was tested by a Hoechst viability assay on human glioma (U-251) and prostate carcinoma (22V1) cell lines, according to the protocol described in the "materials and methods" section above. The results are presented in FIG. 2.

As shown in FIG. 2, Compound 6 is considerably more potent than acyclovir in reducing the viability of U-251 and 22RV1 cell lines. Compound 6 exhibited a significantly greater activity (>100 fold) than acyclovir in both cell lines. The $IC_{50}$ of acyclovir could not be reached.

Compound 6 is expected to readily release the one equivalent of valproate which is bound to acyclovir by an ester bond, and a second valproate moiety bound to the acyclovir by an amide bond is expected to be metabolized considerably more slowly.

To better understand the interaction between acyclovir and valproic acid, the effect of Compound 6 was compared to that of valproic acid (VA) and to that of a mixture of acyclovir and valproic acid (in a 1:2 ratio) in the human leukemic cell line HL-60 and in the human breast carcinoma cell line MCF-7. The results are presented in FIG. 3.

As shown in FIG. 3, VA and the mixture of VA and acyclovir had similar effects on the viability of the cancer cells, whereas Compound 6 was considerably more effective than VA and VA+acyclovir at killing both HL-60 (FIG. 3a) and MCF-7 (FIG. 3b) cancer cells. The IC50 of Compound 6 was over 20-fold lower than that of VA, and over 50-fold lower than that of the mixture of VA and acyclovir, thereby demonstrating that Compound 6 is considerably more potent than its constituents.

As further shown in FIG. 3b, the addition of 400 μM N-acetylcysteine (NAC), an antioxidant, did not reduce the activity of Compound 6, indicating that the release of reactive oxygen species is not involved in the mechanism by which Compound 6 induces death of cancer cells.

In order to better understand the relationship between structure and anti-cancer activity of nucleoside analogs, the effect of N,O-bis-valproyl acyclovir (Compound 6) on U-251 and 22RV1 cells was compared to those of O-mono-valproyl acyclovir (Compound 12) and N-mono-valproyl acyclovir (Compound 23). The results are presented in FIG. 4.

As shown in FIG. 4, N,O-bis-valproyl acyclovir is the most potent compound (IC50=32±2 μM in U-251 cells; 23.2±1.9 μM in 22RV1 cells), followed by O-mono-valproyl acyclovir (IC50=251±12 μM in U-251 cells; 241±12 μM in 22RV1 cells). The IC50 of N-mono valproyl acyclovir was 402±22 μM in 22RV1 cells and above 750 μM in U-251 cells.

These results indicate that both valproyl moieties in Compound 6 contribute to the anticancer activity of the compound, and that the 0-valproyl moiety (i.e. valproyl ester) is more active than the N-valproyl moiety (i.e. valproyl amide).

Apoptosis Measurement by Annexin V-FITC and Propidium Iodide Staining:

In order to elucidate the mechanism by which acyclovir derivatives kill cancer cells, U-251 cells were treated with Compounds 6 and 12 for 24 hours, were stained thereafter with Annexin V-FITC and propidium iodide (PI) and were analyzed by FACS for signs of apoptosis, according to the protocol described in the "materials and methods" section above. Annexin V binds phosphatidyl serine in cell outer membranes, which is a characteristic marker for apoptosis. The results are presented in FIG. 5.

As shown in FIG. 5, both compounds increased the percentage of apoptotic cells in a dose dependent manner, with Compound 6 being considerably more potent than Compound 12.

Assessment of Changes in Mitochondrial Membrane Potential ($\Delta\psi_m$):

The effect of acyclovir derivatives on mitochondrial membrane potential ($\Delta\psi_m$) was examined according to the protocol described in the "materials and methods" section above, as reduction of $\Delta\psi_m$ is an early marker of apoptosis [Levovich et al., 2007]. $\Delta\psi_m$ was examined by staining U-251 cells with JC-1, a mitochondrial dye which exhibits green fluorescence in mitochondria with reduced $\Delta\psi_m$ and red or orange fluorescence in mitochondria with normal $\Delta\psi_m$. The results are presented in FIG. 6.

As shown in FIG. 6, 60 µM of Compound 6 increased the number of mitochondria with reduced membrane potentials, indicating that Compound 6 induces apoptosis, whereas acyclovir and Compounds 12, 22 and 23 had no apparent effect on mitochondrial membrane potential at the same concentration.

Phospho-H2AX Western Blot Analysis:

Increased phosphorylation of ser139 on the histone H2AX is a marker for double-strand breaks (DSBs), which are a sign of apoptosis [Rogakou et al., 1998]. Therefore, the effects of acyclovir derivatives on the levels of phospho-H2AX were investigated using a Western blot, according to the protocol described in the "materials and methods" section above. The results are presented in FIG. 7.

As shown in FIG. 7, Compounds 6 and 22 induced an increase in the level of phosphorylated H2AX. The induced increase reached a peaked after 2 hours of treatment, and was attenuated, most likely due to the high percentage of dead cells, after 24 hours of treatment.

Detection of Reactive Oxygen Species (ROS) and Nitrogen Reactive Species (RNS):

Detection of intracellular reactive oxygen species (ROS) production in U-251 cells was performed by FACS analysis of U-251 cells using the cell-permeable probe, dichlorodihydrofluorescein diacetate, which becomes fluorescent upon oxidation. The results are presented in FIG. 8.

As shown in FIG. 8, Compound 6 considerably increased the level of oxidation in cells, whereas acyclovir and valproic acid, either alone or in combination, had little if any effect.

Sustained production of nitric oxide (NO) acts as a pro-apoptotic modulator by activating caspases [Blaise et al., 2005]. NO oxidative products (e.g. $NO_2$, $ONOO^-$ ions, $HNO_2$, 'NOx') may deaminate, crosslink and oxidize DNA bases eventually leading to cell death. The effect of acyclovir derivatives on NO production was determined according to the protocol described in the "materials and methods" section above. The results are presented in FIG. 9.

As shown in FIG. 9, Compound 6 increased NO production in U-251 cells considerably, whereas a mixture of acyclovir and valproic acid did not have such an effect.

Proteasome Activity Assay:

The proteasome is a multiprotein particle which is the primary component of the protein degradation pathway, central to processes such as cell-cycle regulation, apoptosis, and angiogenesis. Blocking the proteasome proteolytic activity leads to cancer cell death. The anticancer activity of proteasome inhibitors results from stabilization of cell cycle inhibitors, including p21, p27, Bax, p53, I-KB, and the resulting inhibition of NF-KB activation. Consequently, cell cycle arrest is followed by cell death [Corn, 2007]. The effect of acyclovir derivatives on proteasome activity was determined according to the protocol described in the "materials and methods" section above. The results are presented in FIG. 10.

As shown in FIG. 10, 50 µM Compound 6 inhibited proteasome activity in U-251 cells by more 50% after 4 hours, and by more than 75% after 24 hours, whereas acyclovir and valproic acid, alone or in combination, had only a marginal inhibitory effect on proteasome activity. These results indicate that inhibition of the proteasome is an early event having a major contribution to the anticancer activity of Compound 6.

Cell Cycle Analysis:

To examine the manner by which Compound 6 affects the cell cycle, U-251 cells were treated for 24 hours, stained with propidium iodide (PI), and the excitation/emission at 488/600 nm was analyzed by flow cytometry, according to the protocol described in the "materials and methods" section above. The results are presented in Table 2 below.

As shown in Table 2 below, cell-cycle arrest by Compound 6 was evident after 24 hours of treatment. Cell-cycle analysis demonstrated that 1 mM acyclovir arrested the cells in the S phase, 1 mM valproic acid arrested the cells in the $G_2$-M phase, and the mixture of the two arrested the cells in the S-phase. However, Compound 6 arrested the cell cycle in the $G_0$-$G_1$ phase in concentrations of only 25-50 µM, at least 20-fold lower than the concentrations of acyclovir and valproic acid which arrested the cell cycle.

These results indicate that Compound 6 affects cancer cells by a mechanism distinct from that of acyclovir and valproic acid.

TABLE 2

Percentage of cells in each cell cycle stage following treatment

| Cell cycle stage | control | acyclovir (1000 µM) | valproic acid (1000 µM) | acyclovir (1000 µM) + valproic acid (1000 µM) | Compound 6 (25 µM) | Compound 6 (50 µM) |
|---|---|---|---|---|---|---|
| S | 34.0 | 73.6 | 32.5 | 58 | 17.5 | 9.5 |
| G2-M | 36.2 | 12.2 | 47.5 | 34.4 | 33.9 | 13.3 |
| G0-G1 | 29.7 | 14.1 | 20.3 | 7.4 | 48.5 | 77.1 | p21 Western Blot Analysis:

The induction of p21 expression arrests cells in the G1 phase, and is a hallmark of HDAC inhibition [Davie, 2003]. The effects of acyclovir derivatives on p21 expression was determined by Western blot, according to the protocol described in the "materials and methods" section above. The results are presented in FIG. 11.

As shown in FIG. 11, Compound 6 induces expression of the cyclin dependent kinase inhibitor p21 more quickly and to a greater extent than do Compound 12 and acyclovir.

Histone Acetylation:

Inhibition of HDAC induces histone hyperacetylation. The effects of Compound 6 and acyclovir on histone hyperacetylation in U-251 cells were determined by a Western blot for acetylated H4, according to the protocol described in the "materials and methods" section above. The results are presented in FIG. 12.

As shown in FIG. 12, Compound 6 induced acetylation of H4 after 2-4 hours of treatment, whereas acyclovir did not. These observations indicated that Compound 6 was metabolically degraded in the cells to release valproic acid, which acted as an HDAC inhibitor, thereby contributing to the observed anticancer activity.

Viral Thymidine Kinase Activity:

The effect of Compound 6 on the activity of kinases which phosphorylate acyclovir was examined in extracts of 4T1 cells, according to the protocol described in the "materials and methods" section above. The results are presented in FIG. 13.

As shown in FIG. 13, treatment with acyclovir for 24 hours had no effect on the kinase activity, whereas treatment with Compound 6 increased the rate of acyclovir phosphorylation in a significant and reproducible manner.

Anti-cancer Selectivity:

In order to test the ability of Compound 6 to selectively kill cancer cells, the effect of Compound 6 on primary culture of rat astrocytes was compared to its effect on the glioblastoma cell line U-251. Cell death was determined using FACS analysis of cells stained with annexin V-FITC and propidium iodide, according to the protocol described in the "materials and methods" section above. The results are presented in FIG. 14.

As shown in FIG. 14, treatment of glioblastoma cells with 50 μM of Compound 6 for 24 hours increased cell mortality from 9% to 29%, whereas the same treatment did not affect the viability of primary culture of astrocytes. In contrast, treatment of glioblastoma cells with 50 μM of acyclovir for 24 hours increased cell mortality from 9% to 11%, and increased the mortality by necrosis of primary culture astrocytes by 13%. These results indicate that Compound 6 killed cancer cells in a selective manner, having little effect on the viability of normal cells.

Further evidence for the selectivity of Compound 6 towards cancer cells was observed in rat primary cardiomyocytes. Treatment of cardiomyocyte culture for 4 hours with Compound 6 did not increase production of reactive oxygen radicals (ROS), as measured using dichlorodihydrofluorescein diacetate. In addition, treatment of cardiomyocytes with 2 μM doxorubicin (Dox), increased dramatically the production of ROS, whereas the combined treatment of Dox and Compound 6 prevented the formation of ROS. The mixture of VA and acyclovir combined with Dox merely attenuated ROS production induced by Dox. The results indicated that not only was Compound 6 not toxic toward cardiomyocytes, Compound 6 protected cardiomyocytes from ROS production induced by Dox. Moreover, the efficacy of Compound 6 in preventing ROS production in these cells was superior to the effect of the mixture of its components.

In contrast, Compound 6 induced ROS production in cancer cells, as shown in FIG. 7, and discussed hereinabove.

Moreover, Compound 6 acted in synergy with Dox in killing breast carcinoma 4T1 cells. 4T1 cells were treated for 72 hours with Dox, Compound 6 or a mixture of Dox and Compound 6 at a 1:2000 molar ratio, and viability was determined by a Hoechst assay.

As calculated from the results of 3 experiments, the IC50 for Dox was 16.5 nM, the IC50 for Compound 6 was 33.7 μM, and the IC50 for the Dox+Compound 6 mixture was 6.3 nM Dox+12.5 μM Compound 6. The combination index calculated by MEA was 0.75, indicating a synergistic interaction between Dox and Compound 6 in the killing of cancer cells.

The difference in biological activity displayed by Compound 6 towards cancer cells and normal cells (e.g. primary astrocytes and cardiomyocytes) demonstrates a selective lethal activity of Compound 6 towards cancer cells, which is potentially important for selective cancer therapy.

In Vivo Studies:

Acute Toxicity Assay in Mice:

Mice (12 per group) were administered single per os (po) doses of Compound 6 or 7, and their 2 weeks survival rate following treatment was determined, in order to assess the toxicity of Compounds 6 and 7. The results are presented in Table 3.

As shown in Table 3, with the exception of one mouse that died 14 days following treatment with 250 mg/kg dose of Compound 6, no mortality was observed in groups administered up to or 750 mg/kg of Compounds 6 or 7.

These results indicate an LD50 for single doses of Compounds 6 and 7 considerably higher than 750 mg/kg.

TABLE 3

Acute toxicity in ICR mice following administration of a single per os dose of Compounds 6 and 7

| Single dose (mg/kg) | Survival (%) Compound 6 | Survival (%) Compound 7 |
| --- | --- | --- |
| 150 | 100 | 100 |
| 200 | 100 | 100 |
| 250 | 91.8 | 100 |
| 500 | 100 | 100 |
| 750 | 100 | 100 |

Metastatic Lewis Lung Carcinoma Model:

The in vivo anti-cancer efficacy of the acyclovir derivatives was evaluated in a murine metastatic Lewis lung carcinoma (3LL) model. The subclone 3LLD122 of 3LL used in the study was selected for its aggressive and invasive nature. The cells were implanted into the tail vain of C57/BL mice, and 24 hours later they were treated per os thrice per week with Compounds 6 or 7, acyclovir or vehicle. The animals were sacrificed after 21 days of treatment, their lungs were weighed, stained with Bouin's fixative and the metastatic lesions were scored double-blindly.

As shown in FIG. 15, Compounds 6 and 7 showed significant anti-metastatic activity as evidenced by the reduction of the number of lung macro-lesions. A statistical analysis (t-test) confirmed that Compounds 6 and 7 were both significantly (p<0.02) more active than acyclovir in reducing lung metastases.

Metastatic Breast Carcinoma Model:

Compounds 6 and 7 were also tested according to the protocol described in the "materials and methods" section above in an aggressive syngeneic 4T1 murine breast carcinoma model that emulates metastatic stage 1V of the human disease. In this model, treatment commenced after the primary tumor was established (10-12 days after subcutaneous (sc) implantation of the cells). The results are presented in FIG. 16.

As shown in FIG. 16, Compounds 6 and 7 both had an anti-metastatic effect at a dose of 25 mg/kg, as evidenced by a reduction in the number of observed lung lesions and by a reduction in lung weight.

Histone Acetylation:

In order to determine whether HDAC in the 4T1 tumors was inhibited by Compounds 6 or 7, the tumors of the mice were lysed, and histones were extracted and subjected to Western blot analyses, according to the protocol described in the "materials and methods" section above. The results are presented in FIG. 17.

As shown in FIG. 17, tumors from mice treated with Compounds 6 or 7 had significantly higher levels of acetylated H4 than the tumors of mice treated with vehicle only, indicating that Compounds 6 and 7 inhibited the HDAC activity in the tumors. In contrast, a mixture of acyclovir and valproic acid had little effect on H4 acetylation.

The importance of the HDAC inhibitory activity to the anticancer activity of acyclovir derivatives was determined by comparing the efficacy of Compound 7 with the efficacies of Compounds 20 and 8 in a 4T1 breast carcinoma model. Compounds 20 and 8 are lipophilic acyl derivatives of acyclovir like Compound 7, but unlike Compound 7, they lack HDAC inhibitory activity. The results are presented in FIG. 18.

As shown in FIG. 18, Compound 7 had significant anticancer activity, whereas Compounds 20 and 8 had little, if any anticancer activity. These results indicate that the presence of an acyl moiety with HDAC inhibitory activity is important in providing acyl derivatives of acyclovir with anti-cancer activity.

REFERENCES

Bailout M, Germi R, Fafi-Kremer S, Guimet J, Barguès G, Seigneurin J M, Morand P. Real-time quantitative PCR for assessment of antiviral drug effects against Epstein-Barr virus replication and EBV late mRNA expression. *J Virol. Methods.* 2007, 143(1):38-44.

Blaise G A, Gauvin D, Gangal M, Authier S, Nitric oxide, cell signaling and cell death. *Toxicology* 2005, 208:177-192.

Brigden D, Whiteman P. The mechanism of action, pharmacokinetics and toxicity of acyclovir-a review. *J. Infect.* 1983, 6(1 Suppl):3-9.

Chou T C. Theoretical basis, experimental design, and computerized simulation of synergism and antagonism in drug combination studies. *Pharmacol. Rev.* 2006, 58:621-681.

Corn P G. Role of the ubiquitin proteasome system in renal cell carcinoma. *BMC Biochem.* 2007, 8 Suppl 1:S4.

Dachs G U, Tupper J, Tozer G M. From bench to bedside for gene-directed enzyme prodrug therapy of cancer. *Anticancer Drugs* 2005, 16:349-359.

Davie J R. Inhibition of histone deacetylase activity by butyrate. *J. Nutr.* 2003 133:2485 S-2493S.

De Clercq E, Field H J. Antiviral prodrugs—the development of successful prodrug strategies for antiviral chemotherapy. *Br. J. Pharmacol.* 2006, 147:1-11

Herrmann K, Niedobitek G. Epstein-Barr virus-associated carcinomas: facts and fiction. *J. Pathol.* 2003, 199:140-145.

Levovich I, Nudelman A, Berkovitch G, Swift L P, Cutts S M, Phillips D R, Rephaeli A. Formaldehyde-releasing prodrugs specifically affect cancer cells by depletion of intracellular glutathione and augmentation of reactive oxygen species. *Cancer Chemother. Pharmacol.* 2007, Nov. 21 [Epub. ahead of print].

Nudelman A, Levovich I, Cutts S M, Phillips D R, Rephaeli A. The role of intracellularly released formaldehyde and butyric acid in the anticancer activity of acyloxyalkyl esters. *J. Med. Chem.* 2005, 48(4):1042-1054.

Perrine S P, Hermine O, Small T, Suarez F, O'Reilly R, Boulad F, Fingeroth J, Askin M, Levy A, Mentzer S J, Di Nicola M, Gianni A M, Klein C, Horwitz S, Faller D V. A phase ½ trial of arginine butyrate and ganciclovir in patients with Epstein-Barr virus-associated lymphoid malignancies. *Blood* 2007, 109:2571-2578.

Rogakou E P, Pilch D R, Orr A H, Ivanova V S, Bonner W M. DNA double-stranded breaks induce histone H2AX phosphorylation on serine 139. *J. Biol. Chem.* 1998, 273:5858-5868.

Shalitin N, Friedman M, Schlesinger H, Barhum Y, Levy M J, Schaper W, Kessler-Icekson G. The effect of angiotensin II on myosin heavy chain expression in cultured myocardial cells. *In Vitro Cell Dev. Biol. Anim.* 1996, 32(9):573-578.

What is claimed is:

1. A compound having Formula I:

Formula I wherein:
$R_1$ is H;
$R_2$ is an acyl moiety selected from the group consisting of valproyl, 4-phenylbutyryl, cinnamoyl, 2-(4-isobutylphenyl)propionyl, 1-(butyryloxymethoxy)succinyl, 1-(valproyloxymethoxy)succinyl, 1-(4-phenylbutyryloxymethoxy)succinyl, 1-(cinnamoyloxymethoxy)succinyl, 1-(phenylacetoxymethoxy)succinyl and 1-(2-(4-isobutylphenyl)propionyloxymethoxy)succinyl; and
$R_3$ and $R_4$ are each independently hydrogen or an acyl moiety selected from the group consisting of valproyl, 4-phenylbutyryl, cinnamoyl, 2-(4-isobutylphenyl)propionyl, 1-(butyryloxymethoxy)succinyl, 1-(valproyloxymethoxy)succinyl, 1-(4-phenylbutyryloxymethoxy)succinyl, 1-(cinnamoyloxymethoxy)succinyl, 1-(phenylacetoxymethoxy)succinyl and 1-(2-(4-isobutylphenyl)propionyloxymethoxy)succinyl.

2. The compound of claim 1, wherein $R_2$ is selected from the group consisting of 4-phenylbutyryl, cinnamoyl and valproyl, and $R_3$ and $R_4$ are each independently selected from the group consisting of H, 4-phenylbutyryl, cinnamoyl and valproyl.

3. The compound of claim 1, wherein $R_4$ is H.

4. The compound of claim 3, wherein $R_2$ and $R_3$ are each cinnamoyl.

5. The compound of claim 3, wherein $R_2$ is valproyl and $R_3$ is H.

6. The compound of claim 3, wherein $R_2$ is 4-phenylbutyryl and $R_3$ is H.

7. The compound of claim 3, wherein $R_2$ is 2-(4-isobutylphenyl) propionyl and $R_3$ is H.

8. The compound of claim 3, wherein $R_2$ and $R_3$ are each valproyl.

9. N-valproyl-9-(2-valproyloxy) ethoxymethylguanine.

10. A pharmaceutical composition comprising the compound of claim 1 and a pharmaceutically acceptable carrier.

* * * * *